(12) United States Patent
Hansen et al.

(10) Patent No.: US 8,480,760 B2
(45) Date of Patent: Jul. 9, 2013

(54) PASSIVE ANKLE-FOOT PROSTHESIS AND ORTHOSIS CAPABLE OF AUTOMATIC ADAPTATION TO SLOPED WALKING SURFACES AND METHOD OF USE

(75) Inventors: Andrew H. Hansen, Apple Valley, MN (US); Jonathon W. Sensinger, Chicago, IL (US)

(73) Assignees: Northwestern University, Evanston, IL (US); Rehabilitation Institute of Chicago, Chicago, IL (US); Department of Veteran Affairs, Washington, DC (US)

( * ) Notice: Subject to any disclaimer, the term of this patent is extended or adjusted under 35 U.S.C. 154(b) by 0 days.

(21) Appl. No.: 13/066,361

(22) Filed: Apr. 12, 2011

(65) Prior Publication Data
US 2012/0016493 A1     Jan. 19, 2012

Related U.S. Application Data

(60) Provisional application No. 61/342,281, filed on Apr. 12, 2010.

(51) Int. Cl.
    *A61F 2/66*     (2006.01)
(52) U.S. Cl.
    USPC ............................. 623/52; 623/47; 623/50
(58) Field of Classification Search
    USPC ................................. 623/47, 50, 52
    See application file for complete search history.

(56) References Cited

U.S. PATENT DOCUMENTS

| | | | |
|---|---|---|---|
| 1,289,580 A * | 12/1918 | Vincenti | ............ 623/52 |
| 4,360,931 A | 11/1982 | Hampton | |
| 4,413,360 A | 11/1983 | Lamb | |
| 4,547,913 A | 10/1985 | Phillips | |
| 4,555,817 A | 12/1985 | McKendrick | |
| 6,159,248 A | 12/2000 | Gramnas | |
| 6,217,249 B1 | 4/2001 | Merlo | |
| 6,436,149 B1 | 8/2002 | Rincoe | |
| 6,443,993 B1 | 9/2002 | Koniuk | |
| 6,500,138 B1 | 12/2002 | Irby | |
| 7,431,737 B2 | 10/2008 | Ragnarsdottir et al. | |
| 7,637,957 B2 | 12/2009 | Ragnarsdottir | |
| 7,637,959 B2 | 12/2009 | Clausen | |
| 7,811,334 B2 | 10/2010 | Ragnarsdottir | |
| 7,896,927 B2 | 3/2011 | Clausen | |

(Continued)

OTHER PUBLICATIONS

Feldman, Once More on the Equilibrium-point Hypothesis (lambda model) for Motor Control, J. Motor Behav., 18, 1986, pp. 17-54.

(Continued)

*Primary Examiner* — Bruce E Snow
*Assistant Examiner* — Melissa Hoban
(74) *Attorney, Agent, or Firm* — Cook Alex, Ltd.

(57) ABSTRACT

The present invention relates to an improved system for use in rehabilitation and/or physical therapy for the treatment of injury or disease to the lower limbs or extremities. The system can enable an amputee to proceed over any inclined or declined surface without overbalancing. The system is mechanically passive in that it does not utilize motors, force generating devices, batteries, or powered sources that may add undesirable weight or mass and that may require recharging. In particular the system is self-adapting to adjust the torque moment depending upon the motion, the extent of inclination, and the surface topography. An additional advantage of the improvement is that the system can be light and may also be simple to manufacture.

17 Claims, 20 Drawing Sheets

U.S. PATENT DOCUMENTS

| | | | |
|---|---|---|---|
| 2004/0064195 A1 | 4/2004 | Herr | |
| 2004/0153168 A1 | 8/2004 | Childress et al. | |
| 2005/0192677 A1 | 9/2005 | Ragnarsdottir | |
| 2005/0197717 A1 | 9/2005 | Ragnarsdottir | |
| 2006/0030950 A1* | 2/2006 | Townsend et al. | 623/55 |
| 2006/0184280 A1 | 8/2006 | Oddsson | |
| 2006/0224246 A1 | 10/2006 | Clausen et al. | |
| 2006/0224247 A1 | 10/2006 | Clausen | |
| 2006/0249315 A1 | 11/2006 | Herr | |
| 2007/0043449 A1 | 2/2007 | Herr | |
| 2008/0215161 A1 | 9/2008 | Ragnarsdottir | |
| 2009/0222105 A1 | 9/2009 | Clausen | |
| 2010/0030344 A1 | 2/2010 | Hansen | |
| 2010/0185301 A1 | 7/2010 | Hansen | |

OTHER PUBLICATIONS

Perry, Gait Analysis: Normal and Pathological Function, 1992, Slack Inc., 1992.

Latash et al., Joint Stiffness: Myth or Reality?; Hum, Mov. Sci, 12, 1993, pp. 653-692.

Irby et al., Optimization and Application of a Wrap-Spring Clutch to a Dynamic Knee-Ankle-Foot Orthosis, IEEE Trans. Rehabil. Eng., 7, 2, 1999, pp. 130-134.

Ferris et al., Runners Adjust Leg Stiffness for Their First Step on a New Running Surface; J. Biomech.; 32, 8, pp. 787-794, 1999.

Hansen, Roll-over Characteristics of Human Walking With Applications for Artificial Limbs; Dissertation, 2002.

Leroux et al., Postural Adaptations to Walking on Inclined Surfaces: I. Normal Strategies, Gait & Pos., 15, 1, 2002, pp. 67-74.

Lay, The Effects of Sloped Surfaces on Locomotion: A Kinematic and Kinetic Analysis, J. Biomech., 39, 9, 2006, pp. 1621-1628.

Williams et al., Prosthetic Ankle-Foot Mechanism Capable of Automatic Adaptation to the Walking Surface; J. Biomech. Eng., 131, 3, 2009.

Alimusaj at al., Kinematics anfd Kinetics with an Adaptive Ankle Foot System Duting Stair Ambulation of Transtibial Amputees; Gait & Pos.; 30, 3, 2009 pp. 356-363.

Wolf at al., Pressure Characteristics at the Stump/Socket Interface in Transibital Amputees Using Adaptive Prosthetic Foot; Clin. Biomecha.; 24, 10, 2009, pp. 860-865.

Kangude et al., Single Channel Hybrid EFS Gait System Using an Energy Storage Orthosis: Preliminary Design, Proc. IEEE Eng. Med. Bio. Soc., 2009, pp. 6798-6801.

Fradet at al., Biomechanical Analysis of Ramp Ambulation of Transibital Amputees with an Adaptive Ankle Foot System; Gait & Pos.; 32, 3, 2010, pp. 191-198.

PCT/US2007/022208 International Search Report.

PCT/US2007/022208 Written Opinion of the International Search Authority.

PCT/US2011/000675 International Search Report.

PCT/US2011/000675 Written Opinion of the International Search Authority.

PCT/US2012/000038 International Search Report.

* cited by examiner

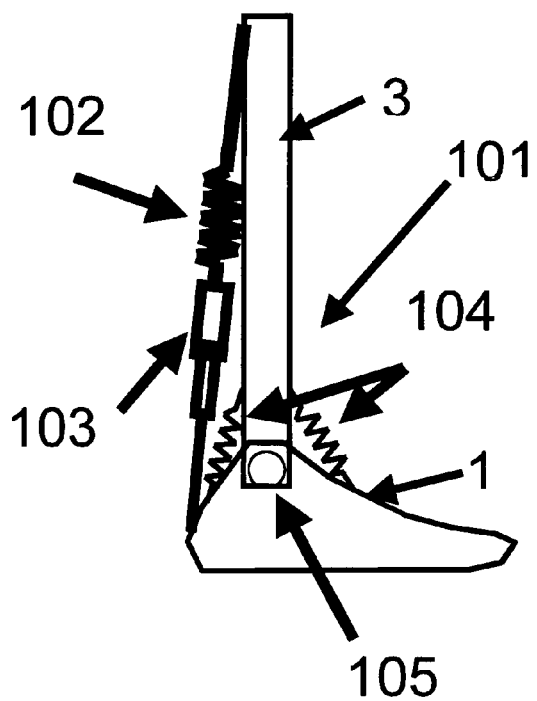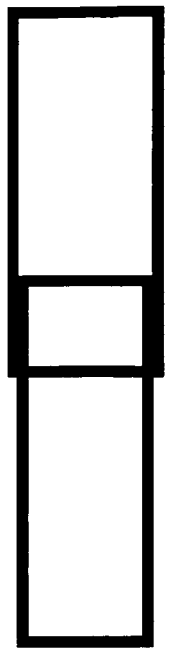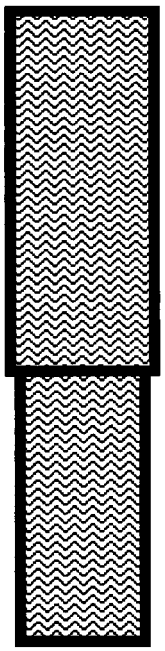
Fig 1    Fig 2a    Fig 2b
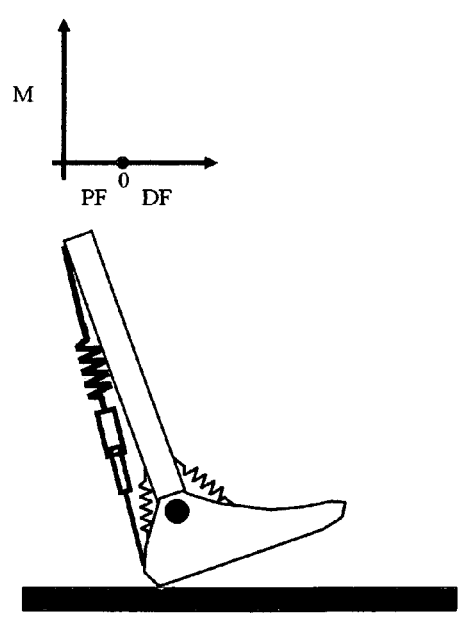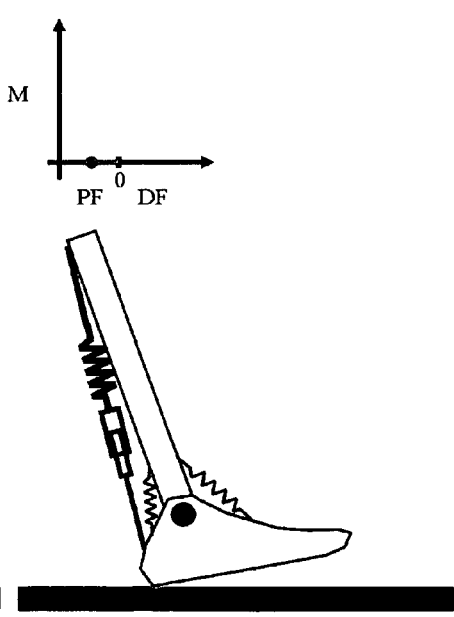
Fig 3A    Fig 3B

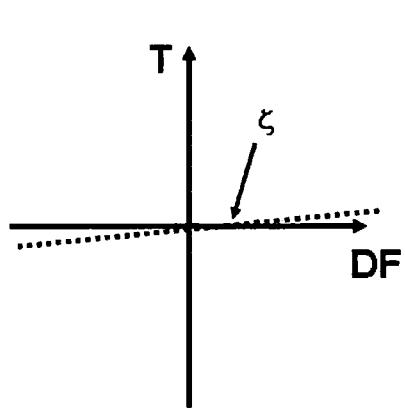
Fig 4
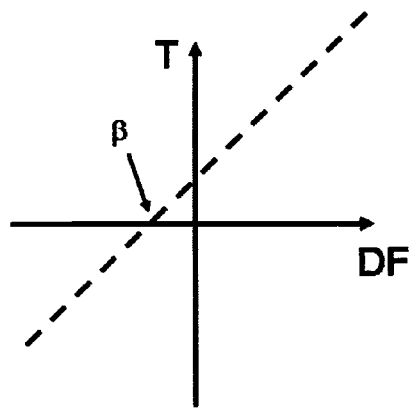
Fig 5
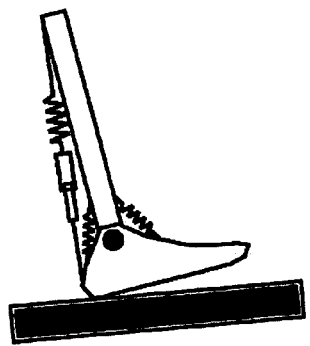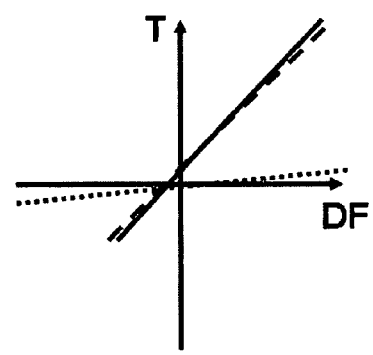
Fig 6A
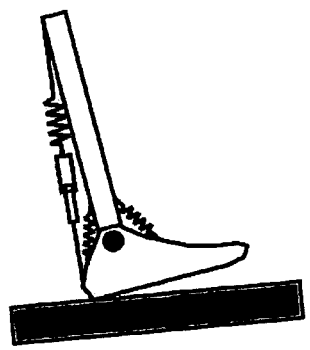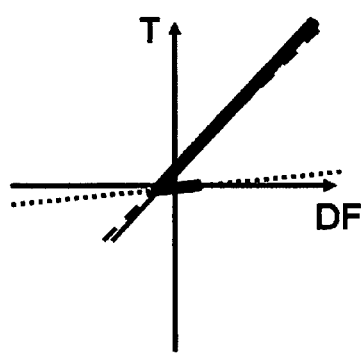
Fig 6B

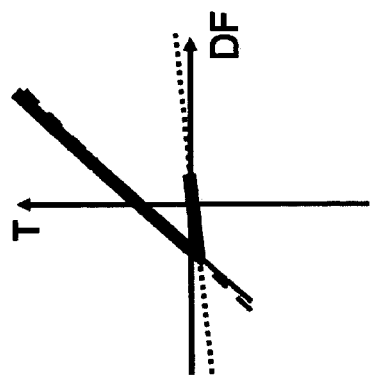
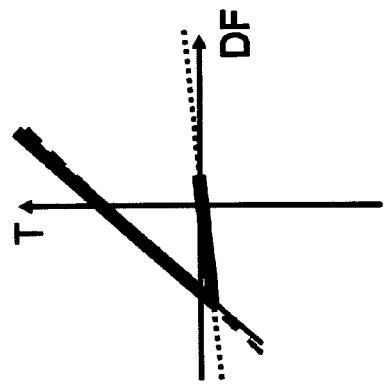
Fig 6C
Fig 6D
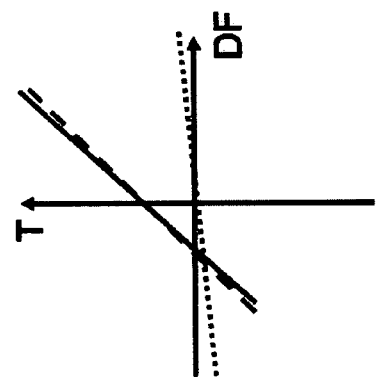
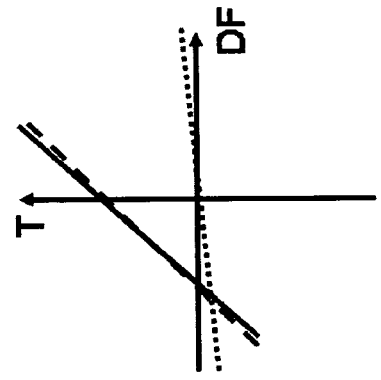
Fig 6E
Fig 6F

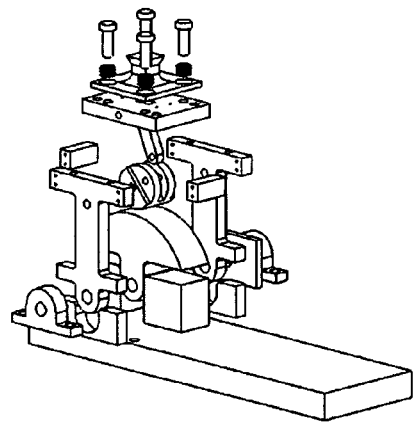
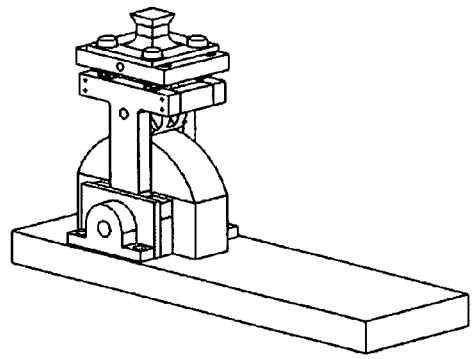
Fig 12A
PRIOR ART
Fig 12B
PRIOR ART
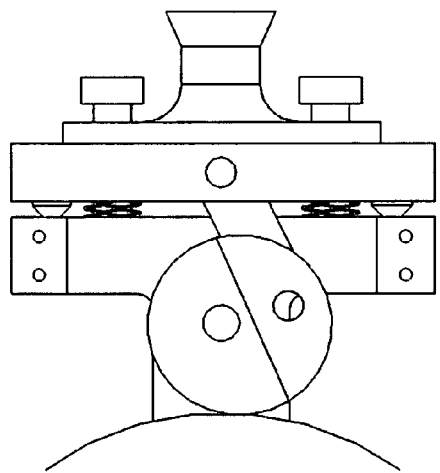
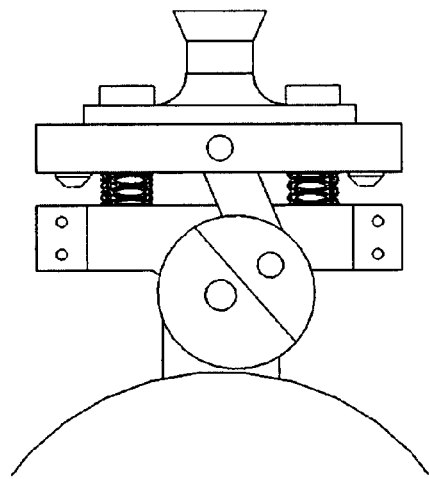
Fig 13A
PRIOR ART
Fig 13B
PRIOR ART

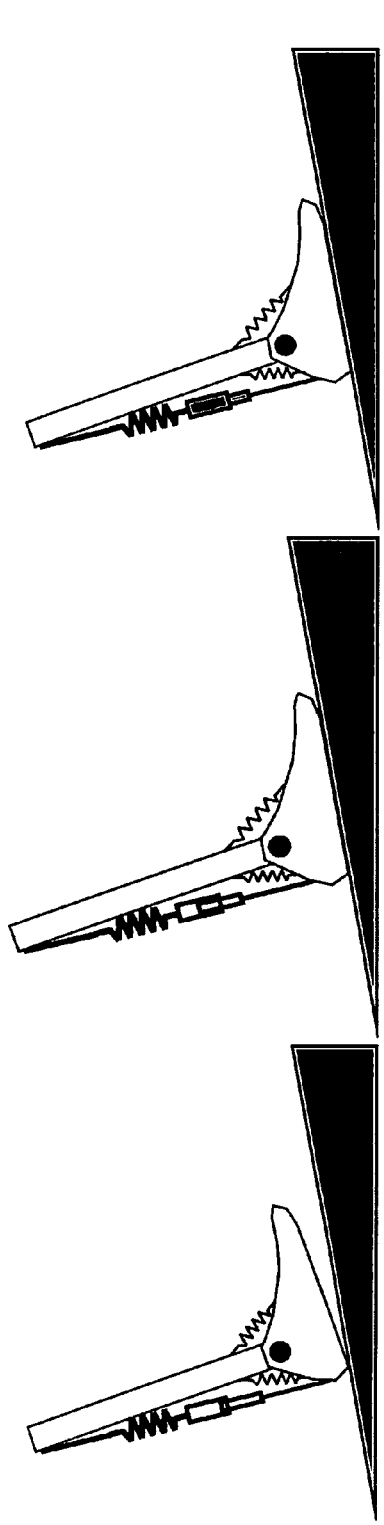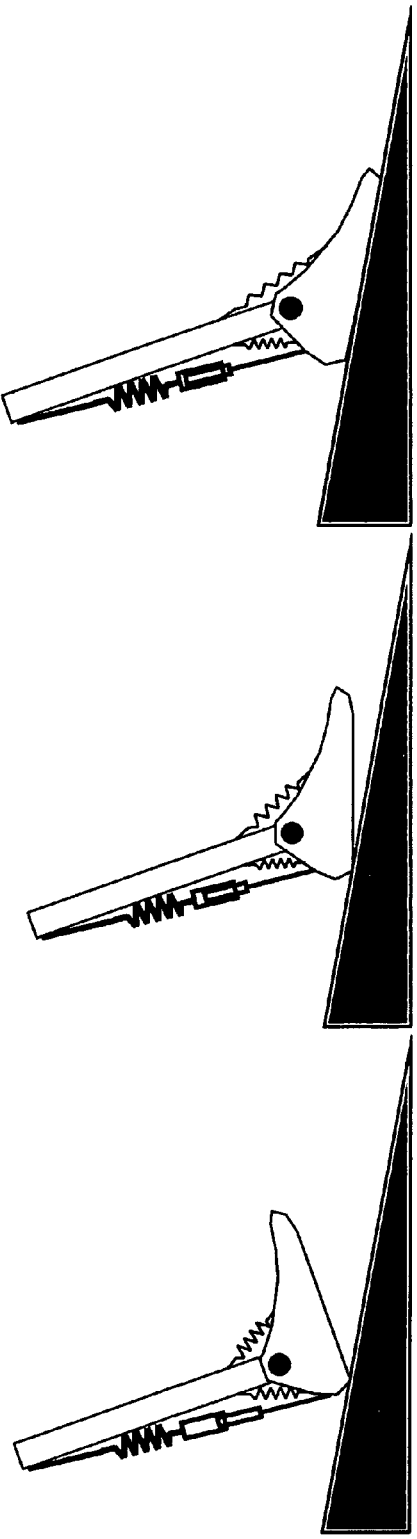

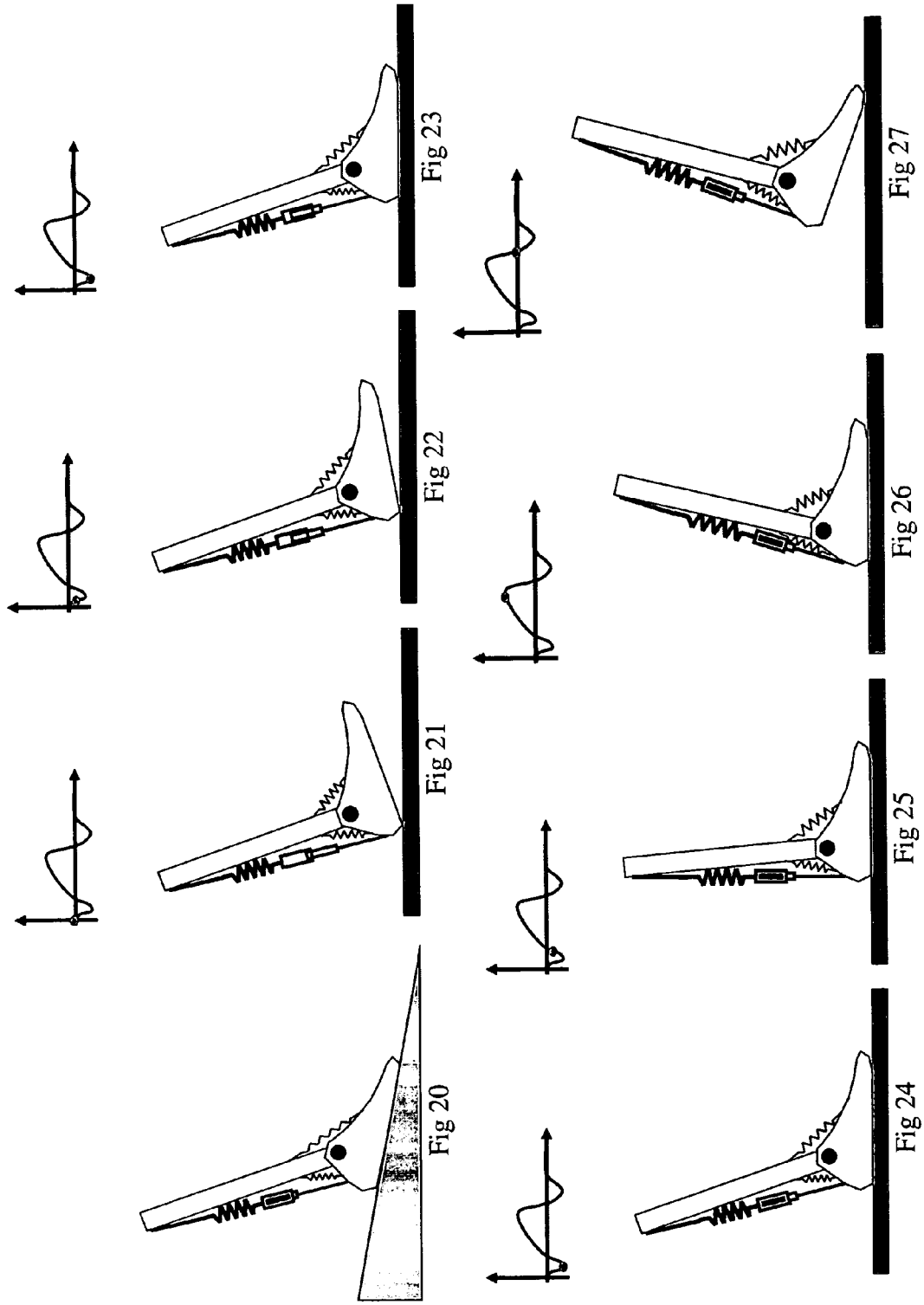

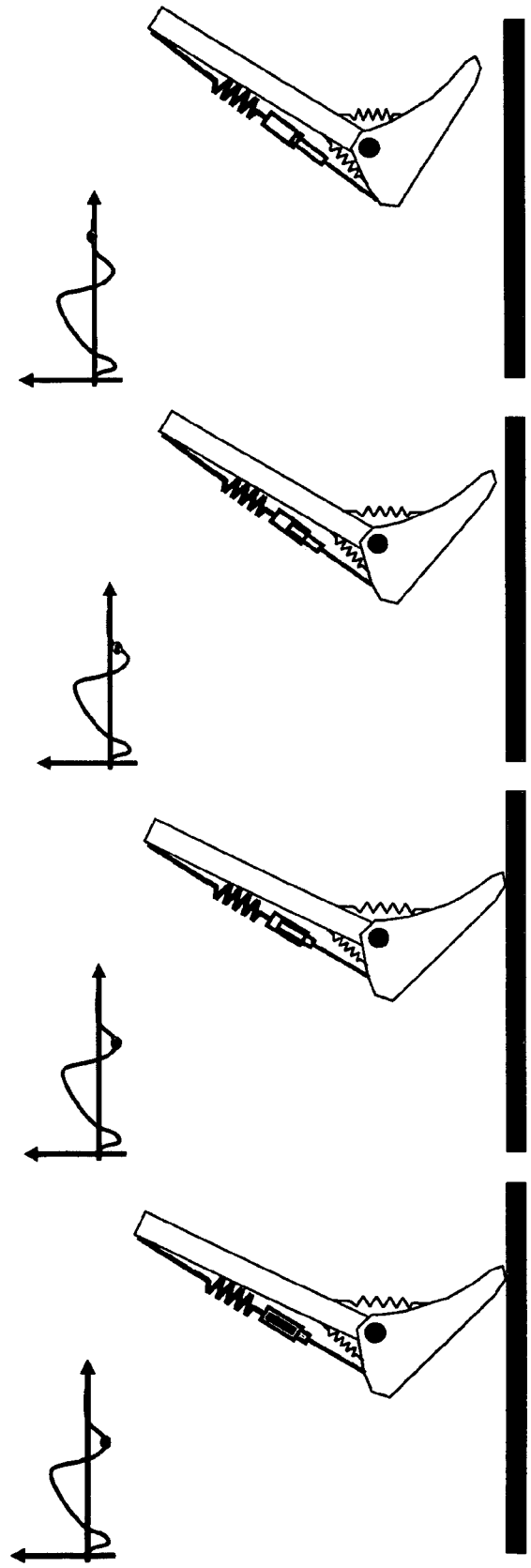

25° Plantarflexion

Neutral

10° Dorsiflexion

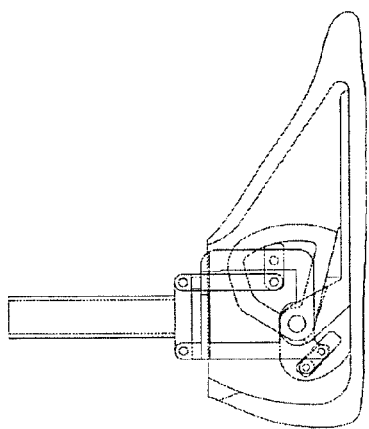
Fig 37A
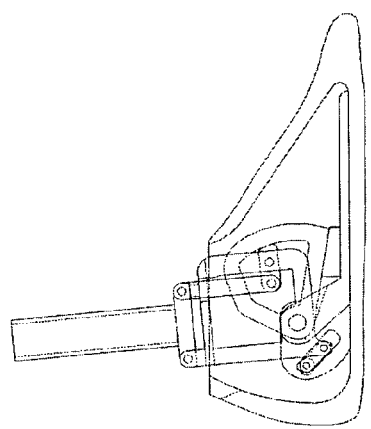
Fig 37B
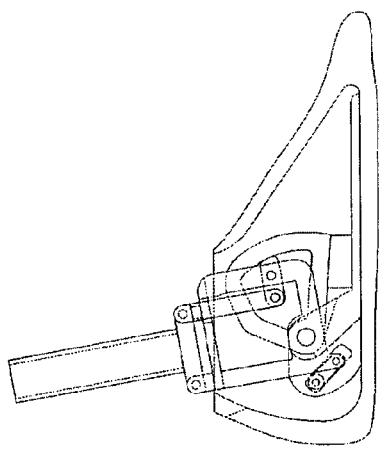
Fig 37C
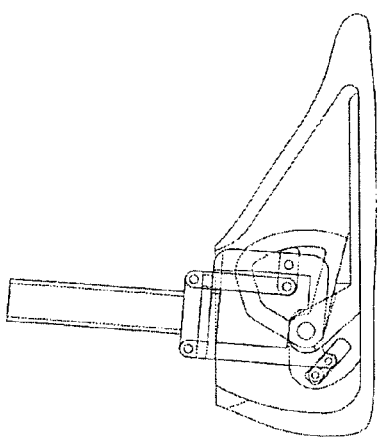
Fig 37D
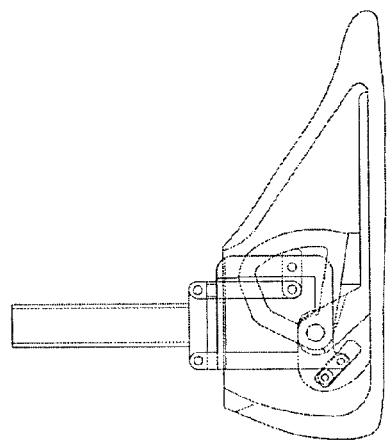
Fig 37E
Fig 37F

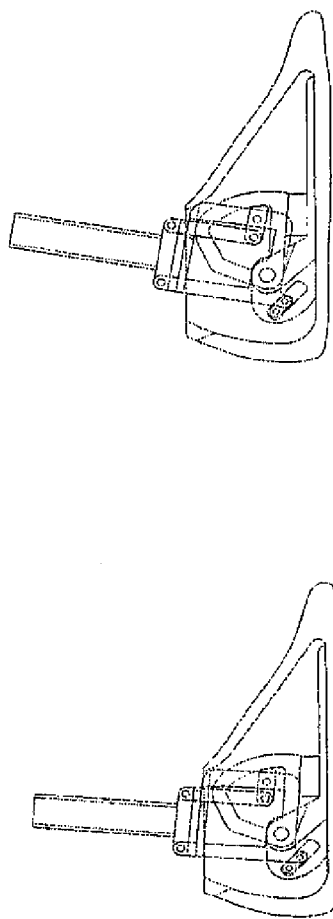
Fig 38D
Fig 38E
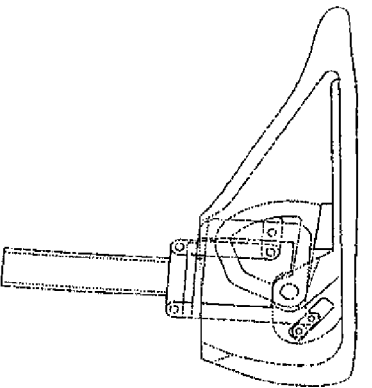
Fig 39C
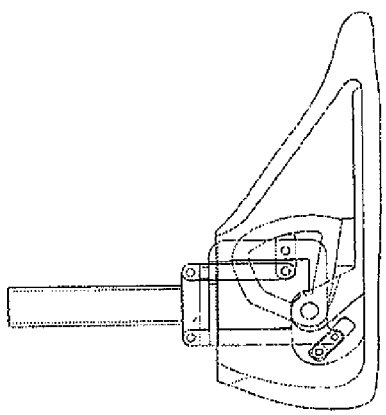
Fig 39B
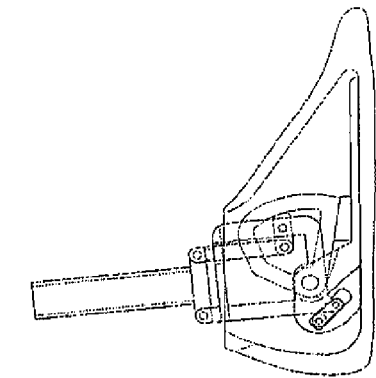
Fig 39A

PASSIVE ANKLE-FOOT PROSTHESIS AND ORTHOSIS CAPABLE OF AUTOMATIC ADAPTATION TO SLOPED WALKING SURFACES AND METHOD OF USE

The present application claims priority to U.S. Provisional Patent Application Ser. No. 61/342,281 entitled "Improvements to Passive Ankle-Foot Prosthesis Capable of Automatic Adaptation to Sloped Walking Surfaces and Methods of Use", filed 12 Apr., 2010, which is herein incorporated by reference in its entirety for all purposes. This application is also related to International Patent Application Serial No. PCT/US2007/022208, filed 17 Oct., 2007, U.S. patent application Ser. No. 12/311,818, filed 13 Apr., 2009, and U.S. Provisional patent application Ser. No. 60/852,174, filed 17 Oct. 2006.

This invention was made with government support under United States Department of Veterans Affairs' grant numbers A6567R and A6565R. The United States government has certain rights in the invention.

TECHNICAL FIELD

The inventions relate to improved ankle-foot prosthetic and orthotic systems and methods of use. In particular the prosthetic or orthotic systems comprise an ankle unit that, in combination with other mechanical elements of prosthetic or orthotic systems, enable the gait of an individual using the device to emulate the gait of able-bodied individual and that automatically adapts the gait to different terrains and slopes on each and every step.

BACKGROUND ART

Many currently available prosthetic and orthotic ankle-foot mechanisms do not allow ankle motion. Rigid ankle prosthetic and orthotic ankle-foot devices generally attempt to replace the actions of the biologic ankle-foot system through deformations of their materials and/or by utilizing rocker shapes on the plantar surfaces. The prosthetic and orthotic ankle-foot devices that do incorporate ankle motion usually allow rotational motion about a single point that does not change without mechanical adjustments of the prosthesis or orthosis. Some of these devices use springs and/or bumpers to store and release energy and return the device's ankle joint to one "equilibrium" point. This single and constant "equilibrium" point can result in good function on level terrain and when using shoes of one particular heel height (heel and forefoot sole differential). However, problems can arise when walking on different terrain or when using shoes of different heel height. The heel height problem can be fixed using a change in the alignment of the prosthesis. However, this is not a simple task and one that does not happen automatically.

A patent issued to Wayne Koniuk (U.S. Pat. No. 6,443,993 B1, "Self-Adjusting Prosthetic Ankle Apparatus", issued Sep. 3, 2002) discloses a device that will adapt to various terrains and to shoes of different heel height. However, Koniuk's design does not appear to have energy storage and release properties, utilizes more sensing devices than the proposed design, and does not appear to give plantarflexion at late stance. Koniuk's design is based on damping control of the ankle joint whereas the proposed device is based on the control of stiffness about the ankle. Damping removes energy from a system whereas stiffness can store and release energy to a system throughout a loading and unloading cycle (that is, a walking cycle).

Recent research has suggested that roll-over shape, the effective rocker shape that the ankle-foot system conforms to between heel contact and opposite heel contact, is an important characteristic for walking. Hansen ((2002); "Roll-over Characteristics of Human Walking With Applications for Artificial Limbs." Ph.D. dissertation, Northwestern University, Evanston, Ill.) found that the able-bodied ankle-foot system adapts to several walking conditions to maintain a similar roll-over shape and that its roll-over shape changes predictably when walking on inclined or declined surfaces. Specifically, able-bodied ankle-foot systems are capable of automatically adapting to differences in shoe heel height and to different surface inclinations. Current prosthetic ankle-foot mechanisms cannot automatically adapt to these conditions.

The prior art demonstrates that there is a current and long-felt need for an improved ankle prosthesis or ankle-foot prosthesis or orthosis that can better emulate the gait of an able-bodied individual and adapt to the terrain on the first step.

SUMMARY OF THE INVENTION

The invention provides prosthetic and orthotic ankle-foot systems. The systems can be used by a human subject as a prosthesis or an orthosis to assist the user's gait and to prevent or reduce the likelihood of compromising the user's balance.

In one embodiment the invention provides a self-adapting prosthetic system, the self-adapting prosthetic system comprising a foot shell, an improved passive adaptive ankle-foot prosthesis, and means for attachment to a leg, the ankle foot prosthesis comprising a footplate, an ankle system, the ankle system comprising a housing, a first cam, a second cam, a bracket, wherein the housing and the bracket are fixedly attached to the means for attachment to the leg, wherein the bracket is fixedly attached to the first cam, wherein the first cam is in movable contact with a part of the second cam and the first cam and second cam comprise a cam clutch system, and wherein the footplate comprises an anterior portion and a posterior portion and further comprising an essentially horizontal plantar member, a torsion means, and an essentially vertical member, the vertical member being perpendicular to the horizontal plantar member and operatively attached to the posterior portion of the footplate, the vertical member further comprising an aperture, the aperture shaped and adapted to confine at least one neutralizing element and a spacer, the neutralizing element being operatively connected to the spacer, wherein the spacer is axially connected to the housing, wherein the housing is axially connected to the vertical member of the footplate, and wherein the second cam is axially connected to the vertical member of the footplate and wherein the torsion means is shaped and adapted for confined placement between the second cam and the horizontal plantar member, and wherein the improved passive adaptive ankle-foot prosthesis is shaped and adapted for placement within the foot shell and wherein the foot shell comprises, in part, a flexible material. In a preferred embodiment, wherein the torsion means is selected from the group consisting of a spring, a tunable spring, a clockwork spring, a piston, a damper, a bumper, and an elastomeric material. In another preferred embodiment the neutralizing element and the cam clutch are in-line. In yet another preferred embodiment, the second cam comprises an external surface and an internal surface. In a more preferred embodiment, the first cam is in movable contact with the internal surface of the second cam. In a most preferred embodiment the range of movable contact of the first cam in contact with the second cam is not greater than 95°. In another most preferred embodiment, the ankle system has a plantarflexion-dorsiflexion range of from between 80° plantarflexion to about 45° dorsiflexion. In another embodiment the ankle system allows a user to emulate normal gait. In an alternative embodiment, the ankle system allows a user to approximately emulate normal gait.

In another preferred embodiment the self-adapting prosthetic system comprises a composition selected from the group consisting of stainless steel, copper, aluminum, titanium, metal matrix composite, metal alloy, NITINOL, DELRIN (acetal), acrylonitrile butadiene styrene (ABS), nylon, polypropylene, polybromate, polycarbonate, glycolised polyethylene terephthalate (PETg) copolyester, polytetrafluorethylene (PTFE), ePTFE, polypropylene, a polymer, glass fiber-resin composites, and carbon fiber resin composites. In an alternative embodiment the self-adapting prosthetic system further comprises a foot shell. In a preferred embodiment, the means for attachment to a leg are selected from the group consisting of a residual limb socket, direct skeletal attachment to the residual limb, and a leg cuff.

In another embodiment the invention provides a self-adapting orthotic system, the self-adapting orthotic system comprising a footplate, an improved passive adaptive ankle system, and means for attachment to an ankle, the ankle system comprising the footplate, means for attaching to the means for attachment to an ankle, a housing, a first cam, a second cam, a bracket, wherein the housing and the bracket are fixedly attached to the means for attachment to the ankle, wherein the bracket is fixedly attached to the first cam, wherein the first cam is in movable contact with a part of the second cam and the first cam and second cam comprise a cam clutch system, and wherein the footplate comprises an anterior portion and a posterior portion and further comprising an essentially horizontal plantar member, a torsion means, and an essentially vertical member, the vertical member being perpendicular to the horizontal plantar member and operatively attached to the posterior portion of the footplate, the vertical member further comprising an aperture, the aperture shaped and adapted to confine at least one neutralizing element and a spacer, the neutralizing element being operatively connected to the spacer, wherein the spacer is axially connected to the housing, wherein the housing is axially connected to the vertical member of the footplate, and wherein the second cam is axially connected to the vertical member of the footplate and wherein the torsion means is shaped and adapted for confined placement between the second cam and the horizontal plantar member, and wherein the improved passive adaptive ankle-foot orthosis is shaped and adapted for placement on at least one side of the biological ankle of the user or individual. In a preferred embodiment, wherein the torsion means is selected from the group consisting of a spring, a tunable spring, a clockwork spring, a piston, a damper, a bumper, and an elastomeric material. In another preferred embodiment the neutralizing element and the cam clutch are in-line. In yet another preferred embodiment, the second cam comprises an external surface and an internal surface. In a more preferred embodiment, the first cam is in movable contact with the internal surface of the second cam. In a most preferred embodiment the range of movable contact of the first cam in contact with the second cam is not greater than 95°. In another most preferred embodiment, the ankle system has a plantarflexion-dorsiflexion range of from between 80° plantarflexion to about 45° dorsiflexion. In another embodiment the ankle system allows a user to emulate normal gait. In an alternative embodiment, the ankle system allows a user to approximately emulate normal gait.

In another preferred embodiment the self-adapting orthotic system comprises a composition selected from the group consisting of stainless steel, copper, aluminum, titanium, metal matrix composite, metal alloy, NITINOL, DELRIN (acetal), acrylonitrile butadiene styrene (ABS), nylon, polypropylene, polybromate, polycarbonate, glycolised polyethylene terephthalate (PETg) copolyester, polytetrafluorethylene (PTFE), ePTFE, polypropylene, a polymer, glass fiber-resin composites, and carbon fiber resin composites. In an alternative embodiment the self-adapting orthotic system further comprises a foot shell. In a preferred embodiment, the means for attachment to an ankle are selected from the group consisting of a residual limb socket, direct skeletal attachment to the residual limb, a clamshell socket, and a leg cuff.

In another embodiment, the invention provides a prosthetic or orthotic system for a user to emulate normal gait, the prosthetic system comprising an ankle member, the ankle member comprising a reversible engagement means, a first torsion means, and a joint, and wherein in use, a torsion curve plot of ankle moment against ankle dorsiflexion angle of the prosthetic system during a gait cycle comprises at least one transition point, wherein the reversible engagement means is operatively connected to the first torsion means, wherein the first torsion means is operatively connected to the joint, and wherein the joint is operatively connected to the engagement means. In an alternative embodiment, the system allows a user to approximately emulate normal gait. In a preferred embodiment the system is used by a user to proceed over a surface without compromising balance wherein the surface comprises a plurality of grades or elevations. More preferably the torsion curve plot comprises a plurality of transition points. In one alternative embodiment the transition point of the torsion curve plot is at a negative torque moment. In another alternative embodiment the transition point of the torsion curve plot is at a negative ankle dorsiflexion angle. In another alternative embodiment the transition point of the torsion curve plot is at a positive torque moment. In yet another alternative embodiment the transition point of the torsion curve plot is at a positive ankle dorsiflexion angle. In a most preferred embodiment the prosthetic system automatically adapts to different surface conditions. In an alternative embodiment the self-adapting prosthetic or orthotic system further comprises a foot shell In one embodiment the prosthetic system comprises a composition selected from the group consisting of stainless steel, copper, aluminum, titanium, metal matrix composite, metal alloy, such as NITINOL, DELRIN (acetal), acrylonitrile butadiene styrene (ABS), nylon, polypropylene, polybromate, polycarbonate, glycolised polyethylene terephthalate (PETg) copolyester, polytetrafluoroethylene (PTFE), ePTFE, polypropylene, a polymer, glass fiber-resin composites, carbon fiber resin composites, and the like.

In a more preferred embodiment the equilibrium point β of the torsion curve plot is calculated using the equation $$T_{ts}=k_{ts}(\theta-\beta),$$

where $T_{ts}$=torque due to triceps surae spring(s); $\theta$=ankle dorsiflexion angle; $\beta$=ankle angle at the trigger time; and $k_{ts}$ is the impedance factor. In an alternative more preferred embodiment the equilibrium point ζ of the torsion curve plot is calculated using the equation $$T_{ns}=k_{ns}(\theta-\zeta),$$

where $T_{ns}$=torque due to neutralizing spring(s); $\theta$=ankle dorsiflexion angle; $\zeta$=ankle dorsiflexion bias; and $k_{ns}$ is the impedance factor. In another preferred embodiment the method comprises the step of wherein a toe-off and the trigger time occur in continuous and alternating order. In a more preferred embodiment the method provides automatic adaptation in the sagittal plane of the self-adapting ankle-foot device. In another more preferred embodiment the method provides the self-adapting ankle-foot device that adapts to three-dimensional changes in terrain. In a most preferred embodiment the three-dimensional changes in terrain is selected from the group consisting of side slopes, and combinations of side and upward sloping surfaces.

The ankle-foot devices automatically adapt to various walking surfaces using stiffness-based control and few sensing devices. This mode of control may be preferable to damping-based control (Koniuk, 2002) because it allows for return of stored energy. In theory, equilibrium-point prosthetic ankle-foot devices of the invention are designed to store and return energy with a high degree of efficiency.

BRIEF DESCRIPTION OF THE DRAWINGS

FIG. 1 illustrates an exemplary embodiment of the invention.

FIG. 2 illustrates a linear braking mechanism exemplifying the invention.

FIG. 4 illustrates an exemplary torsion curve of a pair of neutralizing springs (NS; prior art) showing ζ, the point of intersection of the curve at T=0 (the equilibrium point).

FIG. 5 illustrates an exemplary torsion curve of a "triceps surae" spring (TS; part of the instant invention) showing β, the point of intersection of the curve at T=0 (the equilibrium point).

FIG. 6 illustrates an exemplary torsion curve of the invention showing that the torsion curve has at least two equilibrium points. FIGS. 6A and 6B exemplify the invention in use up a gradient (slope).

FIGS. 6C and 6D exemplify the invention in use on a level surface. FIGS. 6E and 6F exemplify the invention in use down a gradient (slope or incline/decline). FIGS. 6B, 6D, and 6F illustrate the predicted curve of the invention in use showing the transition point (intersection of the NS curve with the TS curve.

FIG. 11 illustrates two stages during operation of the prosthetic ankle-foot system (inventors' prior art invention) showing, in part, the relative positions of the internal gear and external gear in use.

FIG. 12 illustrates an exploded illustration of an exemplary device of the inventors' prior art invention as well as an exemplary illustration of the device in use.

FIG. 13 illustrates two stages during operation of the prosthetic ankle-foot system (inventors' prior art invention) showing, in part, the relative positions of the base and the cam during active motion of the use. FIG. 13A shows the device in a loaded state. FIG. 13B shows the device in an unloaded state.

FIG. 14 through 20 illustrate a sequence of images of the invention showing how the invention works on inclines and declines.

FIGS. 21 through 31 illustrates a sequence of images of the invention showing how the invention works and discloses plots of ankle dorsiflexion/plantarflexion against time.

FIGS. 37A-O illustrate exemplary sequences of gait cycles at different NS and TS angle values.

FIGS. 37A-37C: Cam engaged at 10° NS plantarflexion. 0-10° TS range shown; FIGS. 37D-37F: Cam engaged at 5° NS plantarflexion. 0-10° TS range shown; FIGS. 37G-37I: Cam engaged at 0° NS plantarflexion. 0-10° TS range shown; FIGS. 37M-37O: Cam engaged at 10° NS dorsiflexion. 0-10° TS range shown.

FIGS. 38A-E illustrate an exemplary gait cycle with 0° TS dorsiflexion and between 10° NS plantarflexion through 10° NS dorsiflexion. FIG. 38A: NS: 10° plantarflexion, TS: 0°; FIG. 38B: NS: 5° plantarflexion, TS: 0°; FIG. 38C: NS: 0°, TS: 0°; FIG. 38D: NS: 5° dorsiflexion, TS: 0°; FIG. 38E: NS: 10° dorsiflexion, TS: 0°.

FIGS. 39A-E illustrate an exemplary gait cycle with 5° TS dorsiflexion and between 10° NS plantarflexion through 10° NS dorsiflexion. FIG. 39A: NS: 10° plantarflexion, TS: 5° dorsiflexion; FIG. 39B: NS: 5° plantarflexion, TS: 5° dorsiflexion; FIG. 39C: NS: 0°, TS: 5° dorsiflexion; FIG. 39D: NS: 5° dorsiflexion, TS: 5° dorsiflexion; FIG. 39E: NS: 10° dorsiflexion, TS: 5° dorsiflexion.

FIG. 40A: NS: 10° plantarflexion, TS: 10° dorsiflexion; FIG. 40B: NS: 5° plantarflexion, TS: 10° dorsiflexion; FIG. 40C: NS: 0°, TS: 10° dorsiflexion; FIG. 40D: NS: 5° dorsiflexion, TS: 10° dorsiflexion; FIG. 40E: NS: 10° dorsiflexion, TS: 10° dorsiflexion.

DETAILED DESCRIPTION OF THE INVENTION

Figures 3C, 3D, 3E:
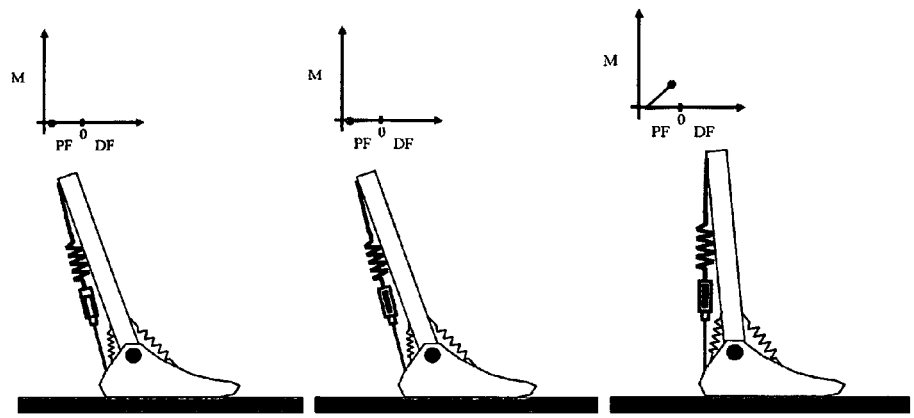
FIG. 3 illustrates an exemplary loading phase of a device of the invention.

The system described herein provides at least three improvements to the inventors' prior art invention.

The inventors were under obligation at the time all the inventors were made to assign the rights to the same entities.

(1) A simpler weight activation element: In the improvement, the prior art four-bolt telescoping system (see, for example, FIGS. 10 through 13, that illustrate inventors' prior art invention) is substituted by a simple hinge (see FIGS. 9, and 34 through 40. The resulting system comprising the simple hinge therefore takes up much less space, is lighter in weight, and is more robust that the prior art.

(2) Improved cam assembly: In the improvement, the cam assembly is greatly reduced in size by moving the drive cam inside the main cam. In addition, the knurls have been omitted that results in quieter operation and a more durable system.

(3) In-line clutch and neutralizing elements: The neutralizing elements and the cam clutch system (comprising the drive cam and the main cam) are positioned in a fore-aft arrangement that allows a much thinner outer housing and having a reduced overall ankle size and ankle thickness. All of these improvements are of benefit to a user.

The equilibrium point prosthetic and orthotic ankle-foot devices work by utilizing a natural movement of the ankle during early stance phase to adjust the resting length, also known as the equilibrium point, of a spring mechanism (see, for example, Williams, et al. (2009) J. Biomechan. Engin. 131: DOI: 10.1115/1.3005335; and PCT/US2007/022208). The devices are named after Feldman's equilibrium point hypothesis ((1986) "Once more on the equilibrium-point hypothesis (lambda model) for motor control" J. Motor Behav. 18: 17-54) regarding the control of human movements. As used herein, the term "equilibrium point" is the angular position of the ankle system when the net external torques (not including those applied by components within the system or in the absence of external forces and moments) are equal to zero.

The premise of the design is the use of two sets of elastic elements, such as a spring or the like, wherein one set dominates the response of the system when an engaging/disengaging mechanism, such as brake or the like, is engaged and another set that dominates the response when the engaging/disengaging mechanism is released. Allowing the foot to "find" the walking surface during early stance and then applying the engaging/disengaging mechanism will allow the device to inherently and automatically adapt to a variety of terrain and/or shoe heel heights. Refer to FIGS. 1-9, 14-30, 32, 34, 35, 36, 37, 38, 39, and 40, for drawings illustrating the embodiment of the invention.

The device comprises two sets of springs: A set of "neutralizing springs" (NS) and a larger and stiffer "triceps surae" spring (TS spring) that is in series with a braking or locking component. The "neutralizing" springs are configured such that their equilibrium point (point of zero ankle moment) is at a point where the ankle is neutral or slightly dorsiflexed (see FIG. 4, at ζ, below). The "triceps surae" spring may be located where the corresponding muscle group (gastrocnemius and soleus muscles) would be (that is, in or proximal to the calf region). This larger and considerably stiffer spring is in series with an engagement means (for example, a braking or locking component) as stated earlier. Preferably, the TS spring and the engagement/disengagement (braking or locking) mechanism, are in series. In the alternative, the TS spring/engagement combination and the NS spring(s) are in parallel. In one embodiment, the engagement mechanism may be considered to be a variable damper that switches between near-zero damping to extremely high damping values.

At all times, the neutralizing springs (ns) are acting according to the following equation ($k_{ns}$, impedance factor; could be a function of θ, the ankle dorsiflexion angle in degrees). This is also an example of the prior art (FIG. 4):

$$T_{ns} = k_{ns}(\theta - \zeta),$$

where
$T_{ns}$=torque due to neutralizing springs
θ=ankle dorsiflexion
ζ=ankle dorsiflexion bias Between the "trigger (engagement) time" to toe-off (the beginning of swing phase), the triceps surae spring (ts) is also engaged according to the following equation ($k_{ts}$, impedance factor, could be a function of θ, the ankle dorsiflexion angle in degrees). This is also an example used to illustrate the instant invention (see, for example, FIG. 5):

$$T_{ts} = k_{ts}(\theta - \beta),$$

where
$T_{ts}$=torque due to triceps surae spring
θ=ankle dorsiflexion
β=ankle angle at the trigger time The ankle angle at the trigger time (β) changes for different terrain: β increases for uphill terrain causing the curve to shift to the right; β decreases for downhill terrain, causing the curve to shift to the left.

For the preferred embodiment, the trigger time is the time of foot flat (in early stance phase). It is conceivable that other trigger times could be used, though, including a time at which the pylori reaches a particular orientation in stance phase (for example, near vertical). So the overall torque at the ankle (T) can be described as follows:

$$T = \begin{cases} T_{ns}; & t_{toe\text{-}off} < t < t_{trigger} \\ T_{ns} + T_{ts}; & t_{trigger} < t < t_{toe\text{-}off} \end{cases}$$

Note that the act of walking is cyclic so the toe-off and trigger times occur in continuous and alternating order. In addition to this, the invention provides not only automatic adaptation in the sagittal plane, but also envisions devices that can adapt to three-dimensional changes in terrain, for example, side slopes, and combinations of side and upward sloping surfaces.

At the transition point, the system engages and sets the equilibrium point of at least one torsional element. This transition switches the system between a low impedance state to a high impedance state. Because the transition point can be tied to a gait event, such as foot flat, the equilibrium point of at least one torsional means can be adjusted in the device, leading to a change in the system's equilibrium point. This adaptability allows for automatic adjustment to different walking surface inclinations.

As shown in FIGS. 6A through 6F, at initial contact of the heel with the walking surface, the brake is unlocked allowing free movement. The neutralizing springs are compressed (and/or stretched) as the ankle moves into a plantarflexed position (that is, as the forefoot comes down to make contact with the floor). During this time, the triceps surae spring remains at its resting length while the braking mechanism changes its length or angle (depending on linear or rotational realization of the device). At the time when the ankle stops moving in the direction of plantarflexion and begins to move into dorsiflexion (that is, at the point of maximum plantarflexion), the braking mechanism locks. This locking action sets the equilibrium point of the triceps surae spring at the point of maximum plantarflexion. As the person rolls forward (during Perry's second rocker (1992) Gait Analysis: Normal and Pathological Function, Thorofare, SLACK Inc.), the triceps surae spring is stretched creating an appropriate ankle moment for walking or the like. After opposite heel contact, the load is removed from the device and the triceps surae spring returns stored energy to the leg by plantarflexing the ankle. When the load is almost fully removed, the ankle will be close to the resting length of the triceps surae spring and the ankle will be at an angle of plantarflexion that is close to that at which the braking mechanism was locked. When the ankle plantarflexion angle comes within a threshold value of the amount that it acquired in early stance, the braking mechanism is released. As the foot leaves the floor in early swing, the neutralizing springs bring the ankle into a neutral or slightly dorsiflexed position (back to position at ζ) to allow for better clearance between the toe and the floor in swing phase. In the alternative, the braking mechanism can be released when a load, such as the weight of the user, is released from being applied to the device.

Improvements of the Invention Over Existing Technologies

The improvements over existing technologies include the ability to adapt to various shoe heel heights and walking inclinations and the provision for plantarflexion at late stance. The device may prove to be superior in energy storing and release characteristics over existing devices although this remains to be seen. Koniuk (2002) has stated the claim of adaptation to shoe heel height and walking inclination in a recently patented design that utilizes damping-control. Our design differs from Koniuk's (2002) in that it utilizes stiffness control and biomimetic foot roll-over shape, allowing the device to achieve an ankle-foot roll-over shape similar to that of an able-bodied person's ankle-foot system during walking, while also allowing for energy return and plantarflexion in late stance.

Design and Manufacture of the Invention

This design is realized in a number of ways. Rotational springs, linear springs, or combinations of the two are used to supply the appropriate impedances about the ankle at different stages of the walking cycle. In the following diagrams, however, the concept of the device will be illustrated using linear springs to describe an "equilibrium-point" prosthetic ankle joint.

FIG. 1 is an exemplary diagram of the device pointing out the various components of the device.

FIG. 2 shows how the linear braking mechanism (that is, linear lock/unlock) is represented in FIG. 3. FIG. 3 shows the action of the ankle-foot device throughout the gait cycle.

FIG. 4, as disclosed above, illustrates a torque curve plot of the prior art using two neutralizing springs (NS). Note that the single equilibrium point at ζ. There is no transition point since there is only one plane of movement.

FIG. 5, as disclosed above, illustrates a torque curve plot using a single "triceps surae" spring (TS). Note the single equilibrium point at β.

FIG. 6 illustrates exemplary torque curve plots of the invention showing that there are two equilibrium points. In FIG. 6, the dotted line represents the predicted torque curve of an NS spring. The dashed line represents the predicted torque curve of a TS spring. The thin solid line represents predicted torque curve of the combination of the NS and the TS. The thick solid line represents an actual torque curve plot showing the transition point ($P_t$). FIGS. 6A and 6B show the invention in use on an incline, FIGS. 6C and 6D show the invention on a level surface. FIGS. 6E and 6F show the invention in use on a decline. FIGS. 6B, 6D, and 6F additionally show the path (heavy line) of a single gait cycle; note the transition point (intersection) of the two torque curves. FIGS. 6B, 6D, and 6F show that the invention can have multiple transition points and that relative position of the transition point on the curve plot is related to the gradient (incline, level, or decline) of the surface. Note also that the torque curve shifts to the left (negative ankle dorsiflexion angle) from going uphill (incline), through level surface, and going downhill (decline).

Figure 7:
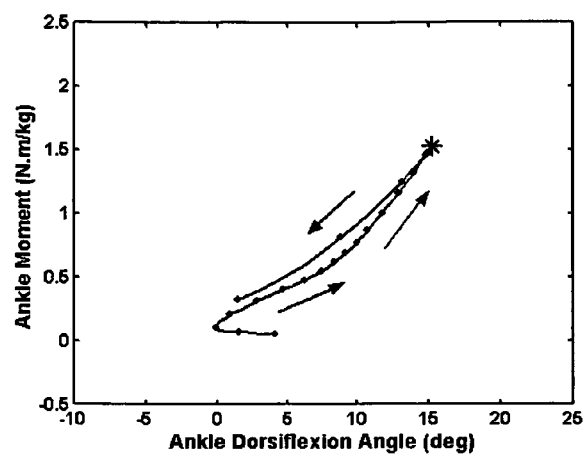
FIG. 7 illustrates average ankle moment plotted against dorsiflexion angle of twenty-four able-bodied subjects.

The springs are chosen to replicate impedance values found for able-bodied human walking (Hansen et al., (2004b) "The Human Ankle During Walking: Implications for Design of Biomimetic Ankle Prostheses and Orthoses" J. Biomech. 37: 1467-1474). These values change somewhat with walking speed but will be designed based on slow to normal walking speeds. The characteristics for extremely fast walking speeds cannot be mimicked using a passive system (Hansen et al., 2004b, supra). A diagram of the ankle impedance characteristics found for twenty four able-bodied ambulators (individuals) is shown in FIG. 7. Notice how this characteristic matches closely the characteristic drawn in the diagrams of FIGS. 3-6 showing that the prosthetic system and the ankle-foot device of the invention automatically adapt to different surface conditions.

Figures 8A, 8B:
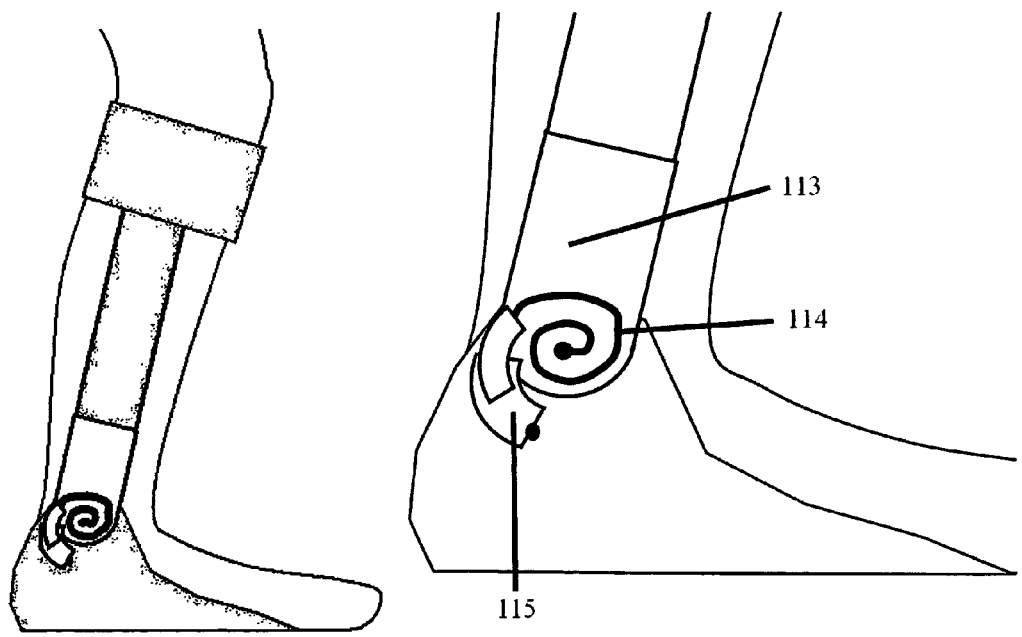
FIG. 8 illustrates an equilibrium-point ankle-foot orthosis (AFO).

This concept can also be used in a rotational sense and in the field of orthoses. An equilibrium-point ankle-foot orthosis (AFO) design that uses rotational components is shown in FIG. 8.

Figure 35:
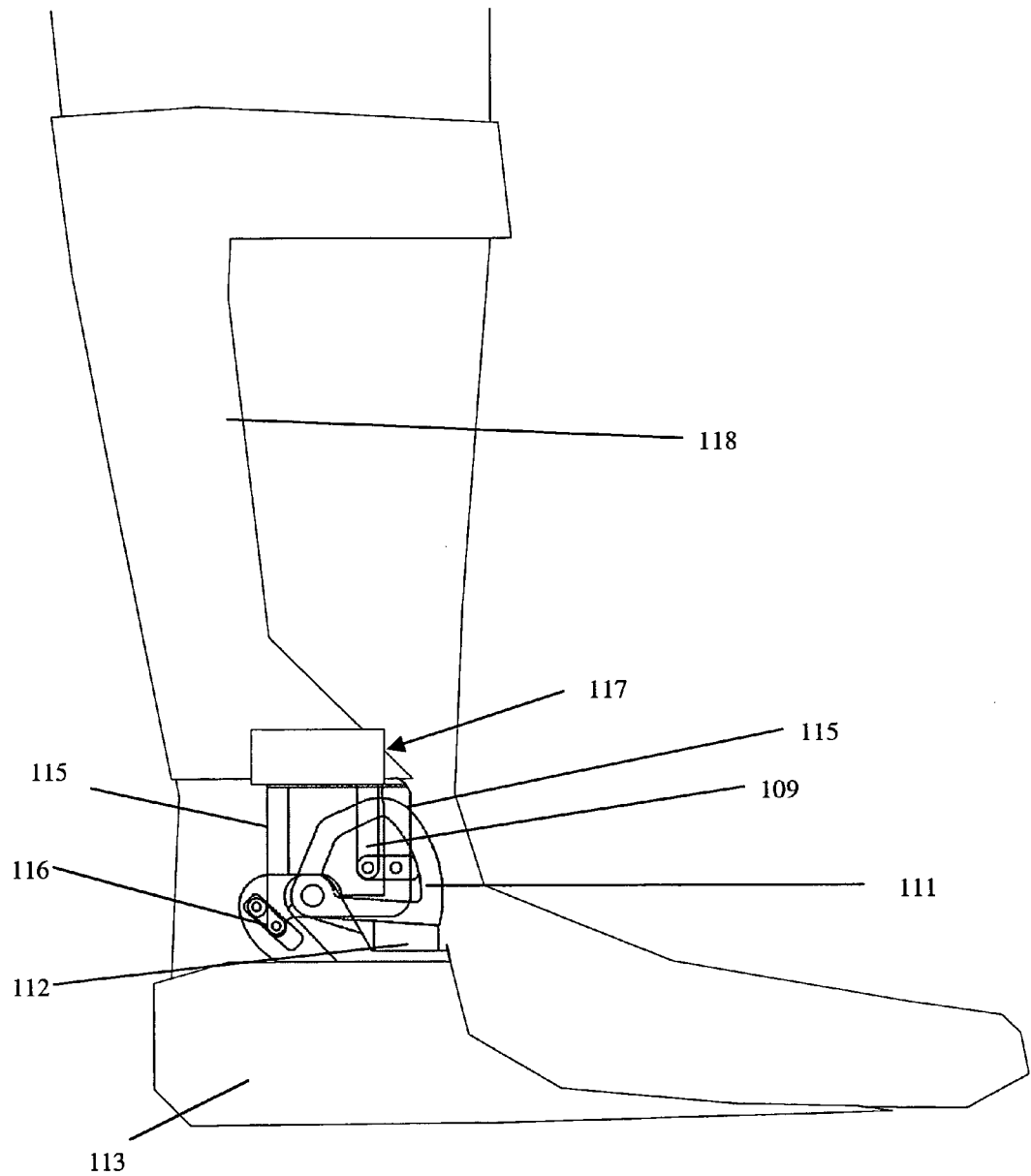
FIG. 35 illustrates an exemplary embodiment of the invention shown wherein the hinge bar and hinge spring are substituted with an actuator (117).
Figure 36:
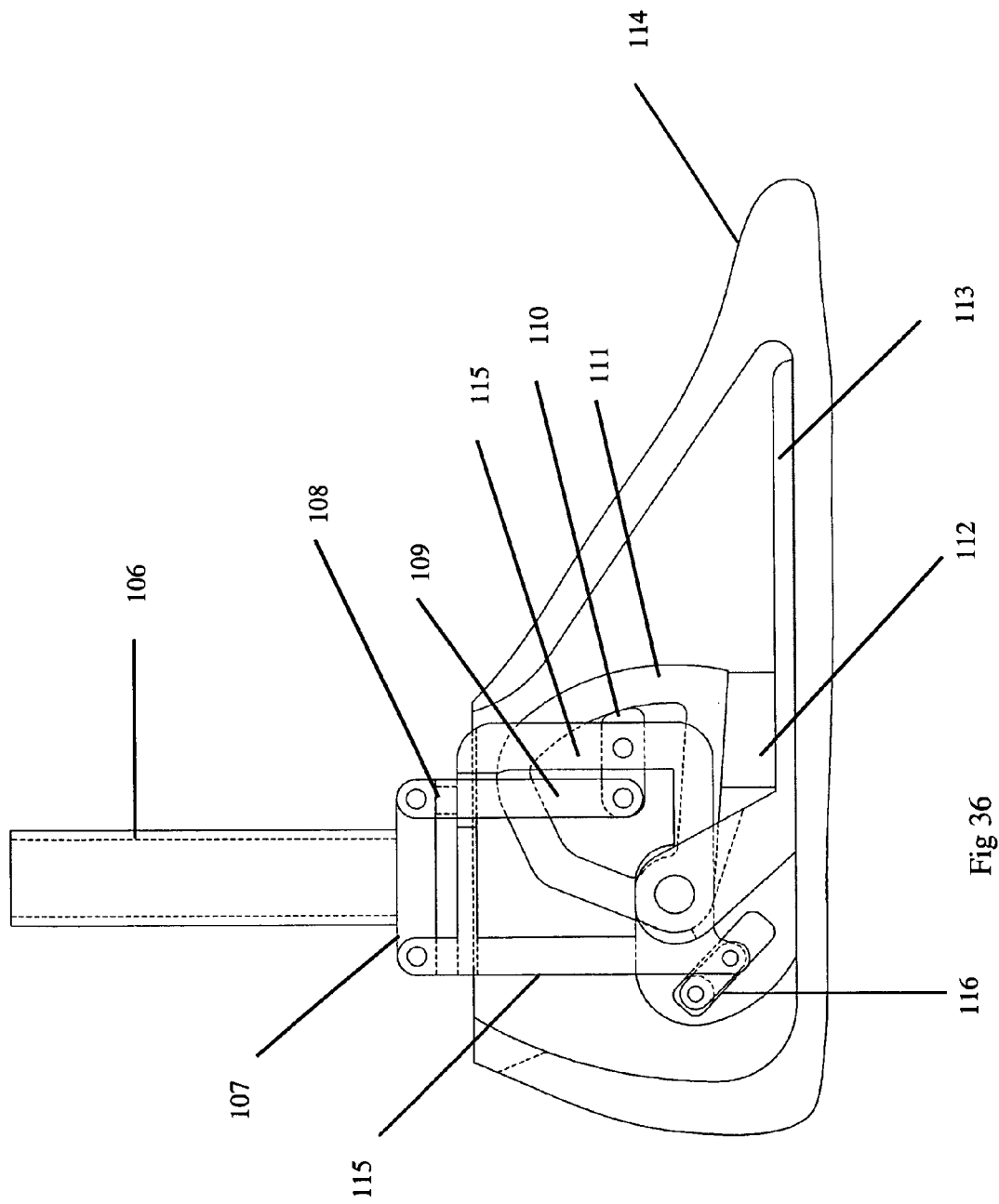
FIG. 36 illustrates an exemplary embodiment of the invention shown when ts=0 and ns=0.
Figure 37H:
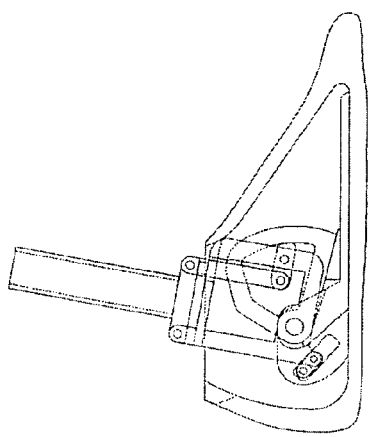
Figure 37L:
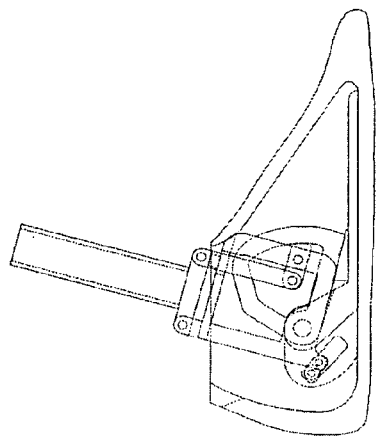
FIGS. 37J-37L: Cam engaged at 5° NS dorsiflexion. 0-10° TS range shown.
Figure 37H:
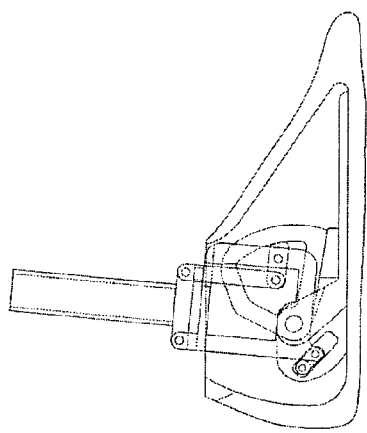
Figure 37K:
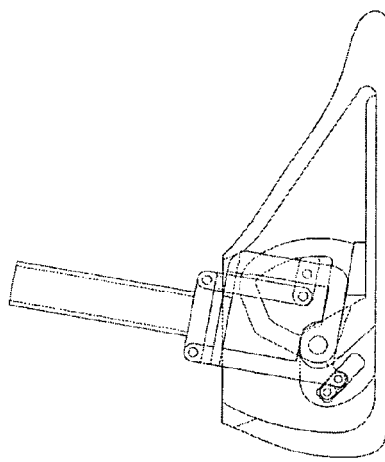
Figure 37G:
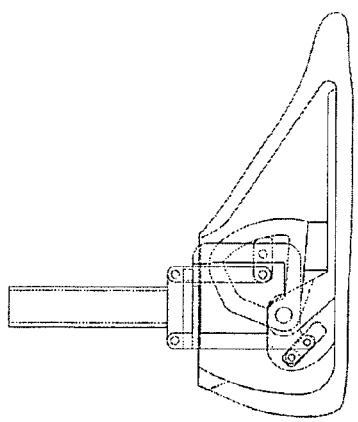
Figure 37J:
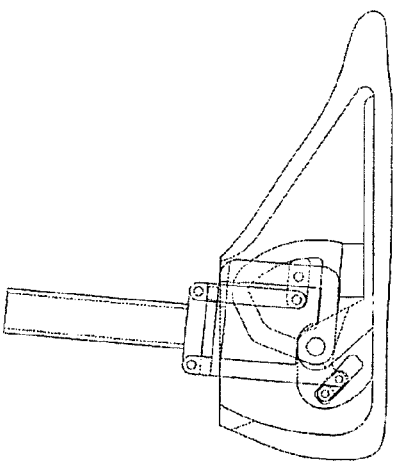
Figure 37O:
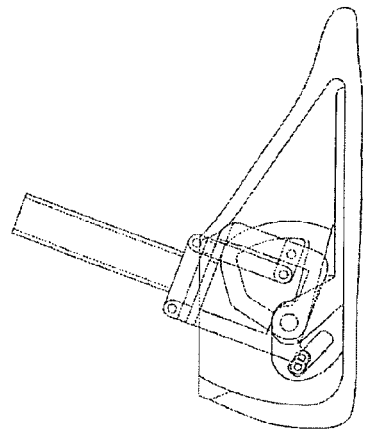

FIGS. 35 and 36 illustrate exemplary ankle systems of the invention showing a pylori (106); a hinge bar (107), a hinge spring (108), a cam engagement link (109), a drive cam (110), a main cam (111), a Triceps Surae Spring (TS) (112), a footplate (113), a foot shell (114), an ankle frame (115), and a Neutralizing Spring (NS) (116), an alternative actuator (117), and means for attachment to a leg (118).

FIG. 35 illustrates an alternative embodiment wherein an actuator moves the descending link. In another alternative, to move the descending link weight activation from beneath the footplate of an orthosis that would interact with the drive cam through an ascending link may be used, wherein the linkage may be restructured to push the drive cam upward during loading. This may be achieved by connecting the posterior pin of the drive cam to the ankle frame and the anterior pin of the drive cam to the ascending link coming up from the footplate load activation system.

FIG. 37 shows exemplary incremental gait cycles where the TS can be from between 0° through 5° through 10°, and where the NS can be from 10° plantarflexion through 0° through 10° dorsiflexion.

Figure 38C:
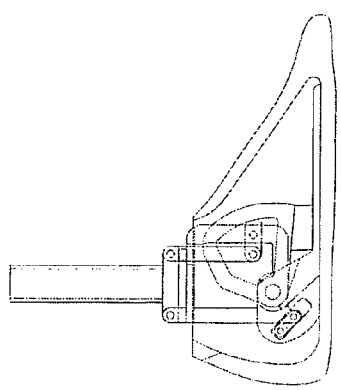
Figure 37N:
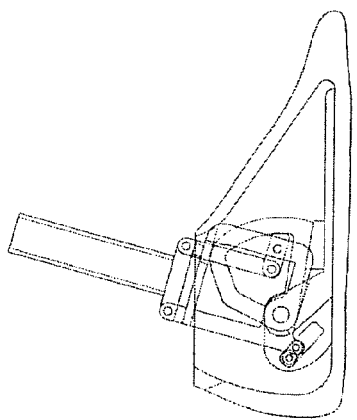
Figure 38B:
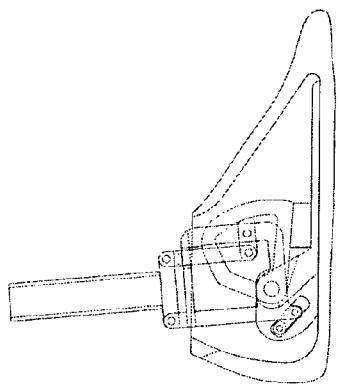
Figure 37M:
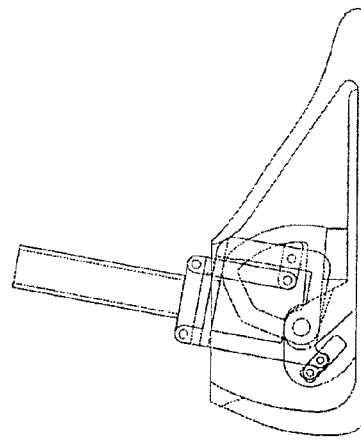
Figure 38A:
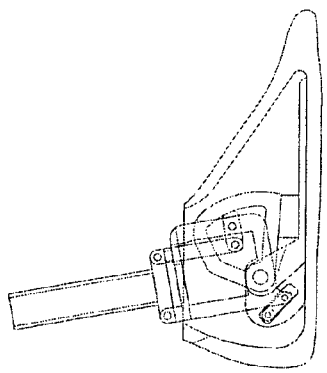
Figure 39E:
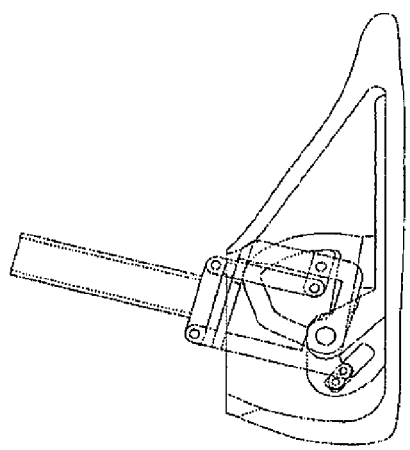
Figure 39D:
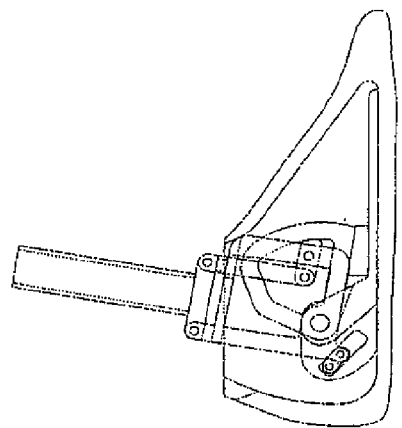
Figure 40C:
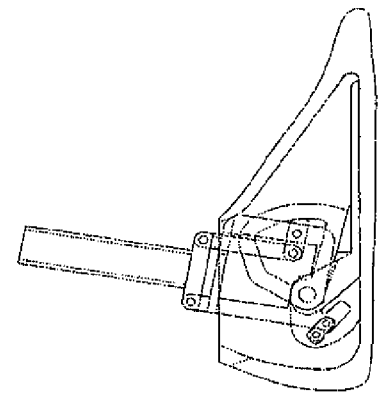
FIGS. 40A-E illustrate an exemplary gait cycle with 10° TS dorsiflexion and between 10° NS plantarflexion through 10° NS dorsiflexion.
Figure 40B:
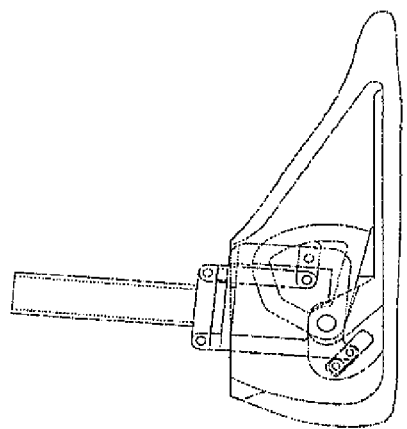
Figure 40A:
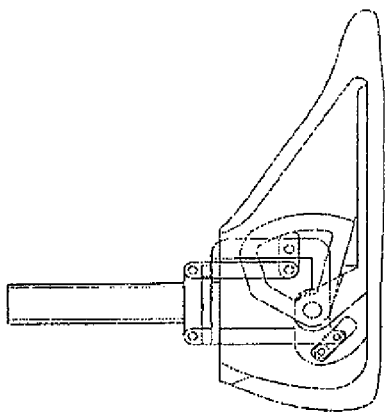
Figure 40E:
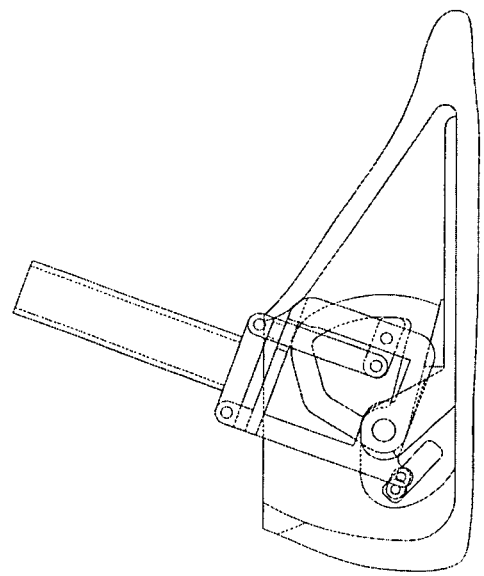
Figure 40D:
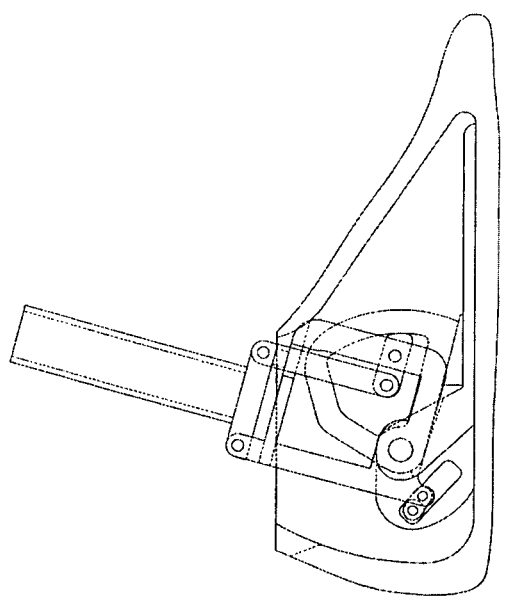

FIGS. 38, 39, and 40 show exemplary incremental gait cycles where the TS can be from between 0° and 10°, and where the NS can be from 10° plantarflexion through 0° through 10° dorsiflexion.

Exemplary Embodiments of the Invention

In one preferred embodiment, the range of movable contact of the first cam (for example, the drive cam) in contact with the second cam (for example, the main cam) is not greater than 95°. For example, the range of moveable contact can be >0°, 5°, 10°, 15°, 20°, 25°, 30°, 35°, 40°, 45°, 50°, 55°, 60°, 65°, 70°, 75°, 80°, 85°, 90°, and 95° and any angle therebetween.

In another preferred embodiment, the ankle system has a plantarflexion-dorsiflexion range of from between 80° plantarflexion to about 15° dorsiflexion. For example, the range of plantarflexion can be >0°, 5°, 10°, 15°, 20°, 25°, 30°, 35°, 40°, 45°, 50°, 55°, 60°, 65°, 70°, 75°, and 80° and any angle therebetween. In another example, the range of dorsiflexion can be >0°, 1°, 2°, 3°, 4°, 5°, 6°, 7°, 8°, 9°, 10°, 11°, 12°, 13°, 14°, 15°, 16°, 17°, 18°, 19°, 20°, 25°, 30°, 35°, 40°, and 45° and any angle therebetween. Where there is neither plantarflexion nor dorsiflexion the ankle system is at 0°, neutral.

The expected commercial applications include ankle-foot prostheses and orthoses for persons with disabilities. These components would hopefully improve the mobility of these persons by allowing them to automatically adapt to various walking surfaces while at the same time giving them biomimetic ankle-foot roll-over shape as well as storage and release of energy from the prosthesis at the appropriate times. The device can also allow for automatic adaptation for different heel heights, allowing a user to use a variety of different shoes. The devices can also be used in walking machines, legged robots, and toys.

The prosthetic or orthotic foot can be manufactured from a variety of compositions and a variety of combination of compositions. The prosthetic foot can comprise a composition selected from the group consisting of stainless steel, copper, aluminum, titanium, metal matrix composite, metal alloy, such as NITINOL, DELRIN (acetal), acrylonitrile butadiene styrene (ABS), nylon, polypropylene, polybromate, polycarbonate, glycolised polyethylene terephthalate (PETg) copolyester, polytetrafluorethylene (PTFE), ePTFE, polypropylene, or another polymer, glass fiber-resin composites, other composite materials, and the like, and, optionally, that can be easily machined, compression molded, or injection molded to the required shape.

The prosthetic foot can be shaped and sized for purposes of mass manufacture in a standard size and shape. In the alternative, it can be manufactured to specifications for a single individual. The prosthetic foot can be manufactured using modular components, the modular components having different shapes, sizes, and compositions.

The ankle of the prosthetic foot can comprise a locking mechanism, for example the locking mechanism can be selected from the group consisting of, a pair of cams, a ratchet mechanism, a ball joint (such as disclosed in U.S. Pat. No. 6,217,249 to Merlo, issued Apr. 17, 2001), selectively engageable and disengagable mechanisms, and joint locking mechanisms as disclosed in, for example, U.S. Pat. No. 6,159,248 to Gramnas, issued Dec. 12, 2000, U.S. Pat. No. 6,436,149 to Rincoe, issued Aug. 20, 2002). The prosthetic system can also be combined with at least one microprocessor comprising a software program or other instructional means that in combination can provide a control means. The control means can measure the torsion within the system and/or the angular movement of the ankle and thereby control the engagement means and the torsional means during each step cycle or gait cycle. Such microproccessors and software programs are well known to those of skill in the art.

There now follows a non-exhaustive list of different devices and/or mechanisms known to those of skill in the art that can be used with the invention.

Engagement Means

Types of Clutch

Automatic clutch, backstopping clutch, ball clutch, bidirectional clutch, brake-clutch combination, cam clutch, cam and roller clutch, centrifugal clutch, cone clutch, detent slip clutch, disc clutch, dog clutch, double clutch, double-spring clutch, dual-spring slip clutch, duplex clutch, driving clutch, eddy current clutch, electrostatic clutch, expanding shoe clutch, externally controlled positive clutch, external control clutch, internal control clutch, fixed-field clutch, fluid clutch, free-wheeling clutch, friction clutch, multiple disc clutch, détente clutch, plate clutch, hysteresis clutch, indexing clutch, internally controlled clutch, jaw clutch, lawnmower clutch, bidirectional locking clutch, locking clutch, magnetic friction clutch, magnetic particle clutch, magnetic fluid clutch, magnetostrictive clutch, mechanical clutch, mercury-gland clutch, multidisk clutch, multistation clutch, one-way clutch, overload relief clutch, overriding clutch, overrunning clutch, planetary transmission clutch, plate clutch, roller clutch, roller clutch, rotating-field clutch, sliding-key clutch, slip clutch, spiral-band clutch, sprag clutch, spring clutch, spring and ball radial detent clutch, station clutch, tooth clutch, torque limiting clutch, trip clutch, wedging ball or roller clutch, and wrap spring clutch.

Types of Brake

Air brakes, anti-lock brakes, coaster brakes, disc brakes, drum brakes, eddy current brakes, electric brakes, friction brakes, hub brakes, hydraulic brakes, multi-disc brakes, power brakes, rim brakes, spoon brakes, band brakes, and caliper brakes.

Types of Lock

Cruciform lock, cylinder lock, deadbolt lock, disc tumbler lock, electronic lock, magnetic lock, electric strike lock, level tumbler lock, Chubb detector lock, protector lock, padlock, pin tumbler lock, wafer tumbler lock, warded lock, 5 lever lock, keycard lock, rim lock, combination lock, and pin lock.

Torsional Means

Types of Spring

Coil or helical spring, tension spring, compression spring, leaf spring, v-spring, spiral spring, clock spring, cantilever spring, Belleville washer spring, spring washer, torsion spring, gas spring, rubber band, elastic elements, bumpers, umbrella springs, conical springs, taper springs, disc spring, and extension spring.

Types of Damper

Backdraft damper, barometric damper, butterfly damper, curtain damper, dual tube damper, flap damper, free-piston monotube damper, guillotine damper, louvre damper, sliding damper, and vibration damper.

| REFERENCE NUMERALS | |
|---|---|
| 1. | Foot member |
| 2. | Bearing |
| 3. | Arm |
| 4. | First cam |
| 5. | Spacer |
| 6. | Spring or second bumper (Torsion means) |
| 7. | Block |
| 8. | Set screw |
| 9. | Second cam (Engagement means) |
| 10. | Spring or first bumper (Torsion means) |
| 11. | First shaft |
| 12. | Second shaft |
| 13. | Third shaft |
| 14. | Fourth shaft |
| 15. | First aperture |
| 16. | Second aperture |
| 17. | Recess |
| 18. | Link |
| 19. | Housing |
| 20. | Threaded aperture |
| 21. | Bolt |
| 22. | First link aperture |
| 23. | Compression spring |
| 24. | Adaptor |
| 25. | Bolt aperture |
| 26. | First aperture (arm) |
| 27. | Second aperture (arm) |
| 28. | Aperture (first cam) |
| 29. | Surface (adaptor) |
| 30. | Surface (housing) |
| 31. | Bolt aperture (arm) |
| 32. | Internal gear |
| 33. | External gear |
| 101. | Ankle-foot system |
| 102. | "Triceps surae" (TS) spring means |
| 103. | Linear Lock/Unlock means |
| 104. | "Neutralizing" spring(s) means |
| 105. | Ankle Joint |
| 106. | Pylon |
| 107. | Hinge Bar |
| 108. | Hinge Spring |
| 109. | Cam Engagement Link |
| 110. | Drive Cam |
| 111. | Main Cam |
| 112. | "Triceps Surae" Spring (TS) |
| 113. | Footplate |
| 114. | Foot shell |
| 115. | Ankle Frame |
| 116. | "Neutralizing" Spring (NS) |

The invention will be more readily understood by reference to the following examples, which are included merely for purposes of illustration of certain aspects and embodiments of the present invention and not as limitations.

EXAMPLES

Example I

Use of Weight-Activation to Control the Ankle Mechanism

Engagement can be set to occur upon loading of the device by the user's weight. In this case, a mechanism is in place that engages the triceps surae torsional means after a sufficient amount of body weight has been applied to the system. Upon unloading of the device, the engagement reverses (that is the triceps surae spring is disengaged from the rest of the system). Examples of this type of engagement are shown in FIGS. 9, 34, 35, 36, 37, 38, 39, and 40.

Example II

Use of Potentiometers or Encoders to Control Locking-Unlocking Mechanisms

Figure 33:
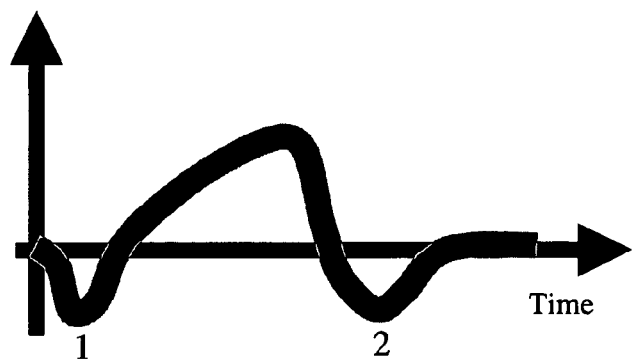
FIG. 33 illustrates a theoretical plot of ankle dorsiflexion/plantarflexion against time for the system or device showing the time at when a first minimum dorsiflexion angle is reached (1) where the brake, lock, or clutch engages and would remain engaged until a second minimum dorsiflexion angle is reached (2).

The projected ankle motion of this device is shown in FIG. 33. The potentiometers or encoders measure these angles during use of the device. In early stance, the locking mechanism may be unlocked. When the rotational sensor indicated that a minimum dorsiflexion angle is reached (at time 1), the system will signal to engage the locking mechanism. This mechanism remains engaged until this angle is approached at the end of stance phase (at time 2), at which time the system unlocks and allows the neutralizing springs to bring the ankle back to neutral for swing phase.

Example III

Use of Forefoot Pressure Sensors to Control Locking-Unlocking Mechanisms

An alternative way to control the locking and unlocking mechanism is to use a forefoot pressure sensor. In early stance, the ankle plantarflexes until the forefoot contacts the walking surface. At this first contact with the forefoot pressure sensor, the locking mechanism may be engaged. Forefoot contact remains until the toe comes off of the ground at the end of stance. At this time, the pressure goes to zero and the locking mechanism could be unlocked, allowing the neutralizing springs to bring the ankle back to neutral for swing phase.

Example IV

Use of Pylori Moments to Control Unlocking of a Cam Mechanism

Devices to measure moments on the pylori maybe used to indicate the time at which a cam locking mechanism should be unlocked. The cam mechanism disclosed herein automatically sets the equilibrium point of the ankle in early stance but needs a control signal at late stance to release the cam. After the middle cam is engaged and the front bumper is compressed, a moment is produced on the pylori that can be measured. After the load is removed from the leg, this moment should go to zero. Thus a circuit or microprocessor could note the falling edge of a pylori moment and use this falling edge as a trigger to unlock the cam mechanism after toe off.

FIG. 1. Illustration of the "Equilibrium-Point" Prosthetic Ankle Joint.

FIG. 2. The linear braking mechanism (that is, "linear lock/unlock") is shown in the following figures as clear when it is unlocked and is shown in gray shading when it is locked.

FIGS. 3A, 3B, and 3C. The initial loading phase for the device. The braking mechanism is unlocked allowing the foot to be lowered to the floor against the resistance of the neutralizing springs. This action mimics what Perry (1992, supra) refers to as the first rocker or the heel rocker and corresponds to the first double-support part of the gait cycle.

Figures 3F, 3G, 3H:
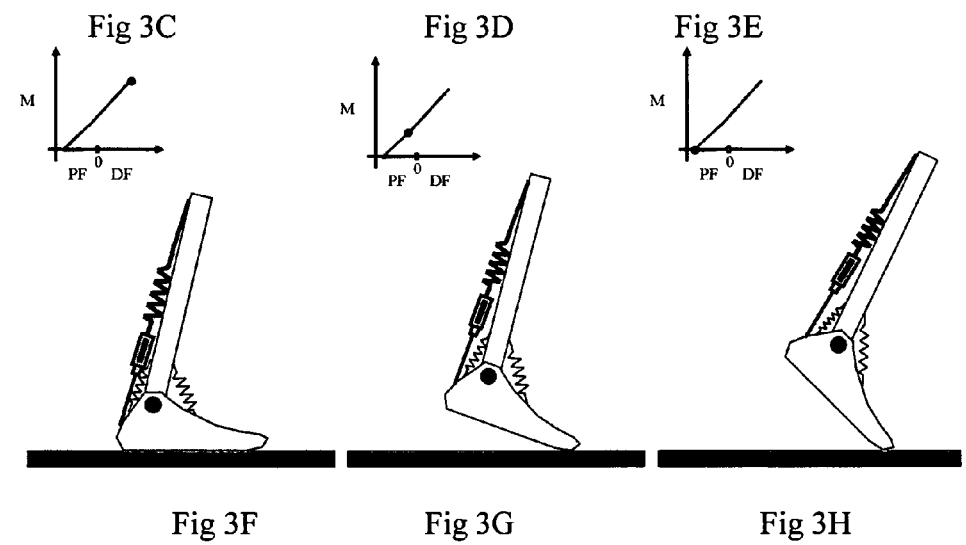

FIGS. 3D, 3E, and 3F. Continuing from FIG. 3C, when the ankle dorsiflexion angle stops decreasing and begins to increase the braking mechanism locks (left). The person then rolls over on the ankle joint as the triceps surae spring is stretched (middle and right). Perry (1992, supra) refers to this as the second rocker or ankle rocker. This period of time corresponds most closely with the single-limb stance period of gait.

FIGS. 3G and 3H. Continuing from FIG. 3F, after the opposite heel contacts (which would be FIG. 3J) the load is rapidly removed from the system and some of the stored energy can be released back to the leg. The series of FIGS. 3G and 3H show this unloading period. At the end of the unloading period, when the dorsiflexion gets near the point where the braking mechanism locked, the brake is released. Perry (1992, supra) refers to this period as the third rocker or the forefoot rocker. This period of time corresponds most closely with the second part of double-limb support of walking.

Figures 3I, 3J, 3K:
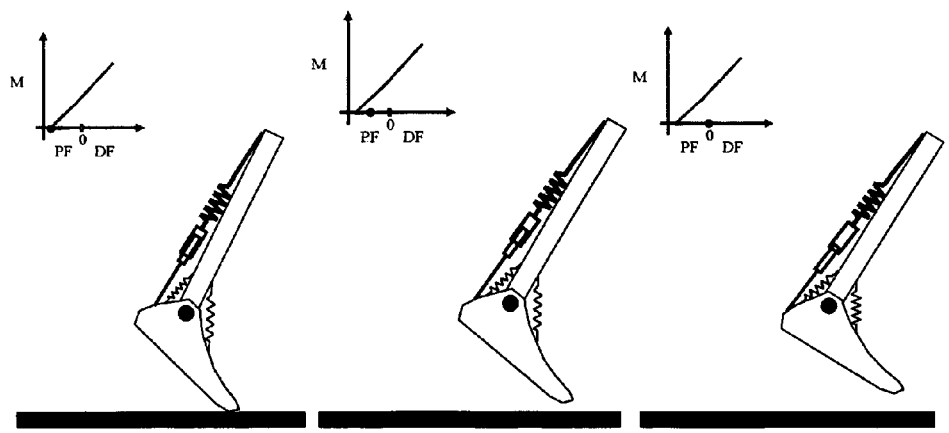

FIGS. 3I, 3J, and 3K. Continuing from FIG. 3H, as the braking mechanism is unlocked the foot is coming off the ground and preparing to swing. In order to avoid stubbing the toes, the ankle needs to go back into a neutral or slightly dorsiflexed position. Since the braking mechanism is unlocked, the neutralizing springs again dominate and pull the foot upwards to a proper position for swing phase.

FIG. 7. Average ankle moment versus dorsiflexion angle plot for 24 able-bodied ambulatory (adapted from Hansen et al., 2004b). Springs will be selected such that the overall impedance of the ankle-foot device mimics this characteristic. The asterisk shows the time at which opposite heel contact occurs. Theoretical ankle moment versus ankle dorsiflexion characteristics for the ankle joint are shown in FIGS. 3-6.

FIG. 8. Equilibrium-point ankle-foot orthosis (AFO). This design is similar to the equilibrium-point prosthetic ankle-foot mechanism except it uses rotational components instead of translational. The neutralizing springs are not shown but are provided by technology that is already available (Klenzak ankle units). These joints can be altered to allow different amounts of dorsiflexion or plantarflexion. They contain spring elements that could act as the neutralizing springs. Other neutralizing joints could also be used. The main elements shown here are the rotational "triceps-surae" spring in series with a rotational lock-unlock mechanism.

Figure 9:
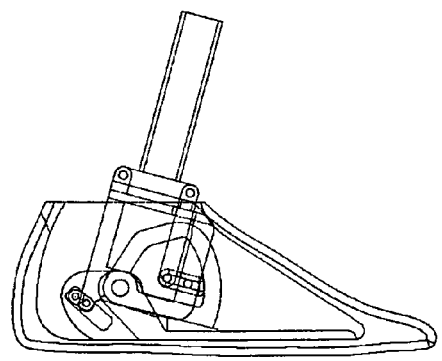
FIG. 9 an exemplary device of the invention.
Figure 10A:
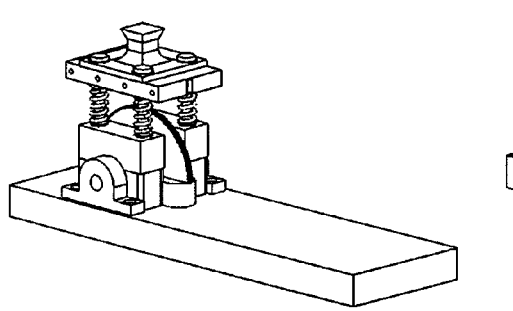
FIG. 10 illustrates an exemplary device of the inventors' prior art invention in use.
Figure 10B:
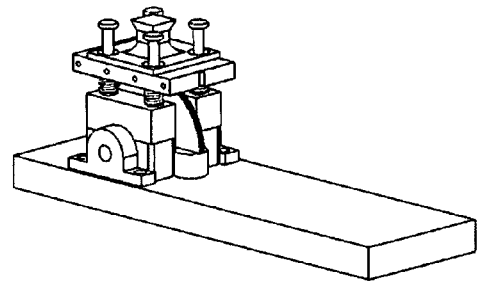
Figure 11A:
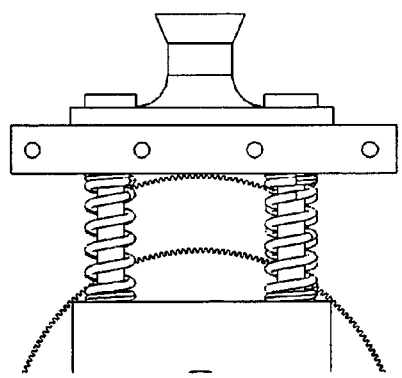
FIG. 11A shows the device in a loaded state.
Figure 11B:
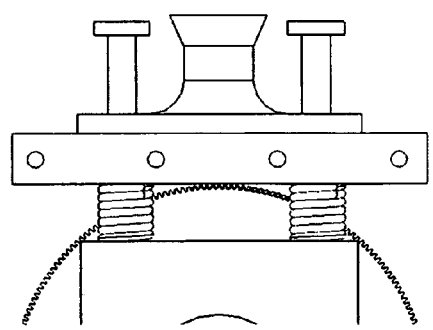
FIG. 11B shows the device in an unloaded state.
Figure 34A:
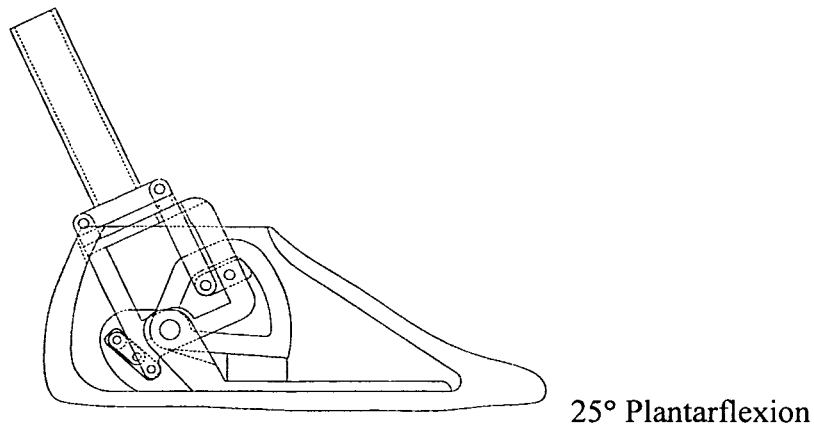
FIG. 34 illustrates three phases of ambulatory motion, (A) plantarflexion, (B) neutral, and (C) dorsiflexion, showing how each of the elements interact with one another.
Figure 34B:
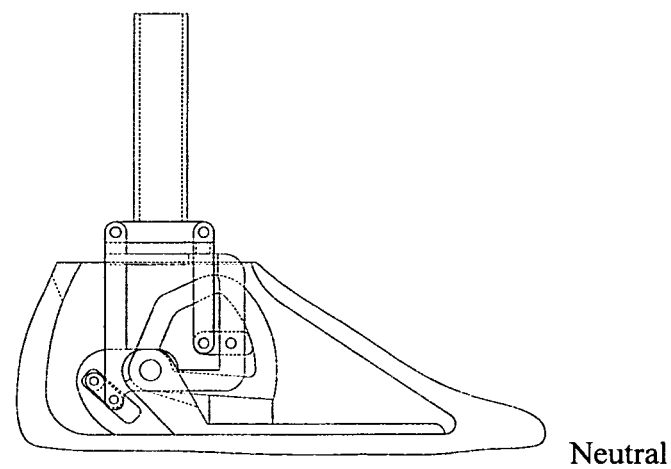
Figure 34C:
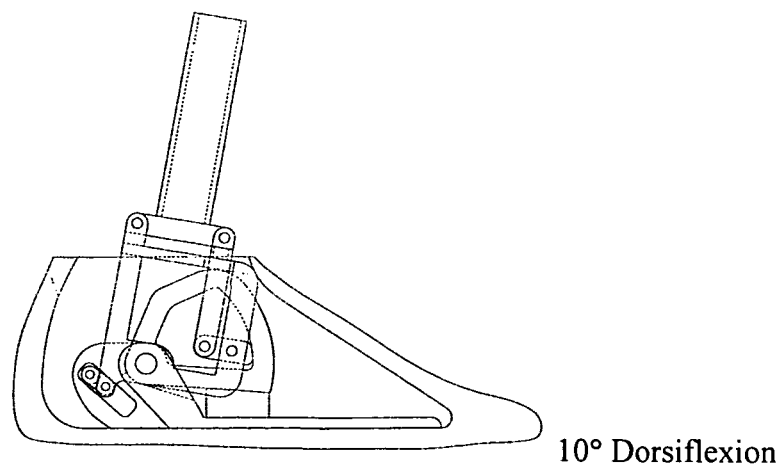

FIG. 9. The improved equilibrium-point prosthetic or orthotic ankle joint device that incorporates a nested drive cam within the main cam, as well as the simple hinge is illustrated. FIG. 34 illustrates the equilibrium-point prosthetic or orthotic ankle joint device in use showing the positions of the simple spring and the drive cam and main cam through a complete exemplary step cycle. Although the cams illustrated have been found to be shaped for optimal function, Applicants submit that many other shapes and positions may also have optimal characteristics. For example, the sites of contact between the two cams may be smaller, or they may be greater than illustrated. The shape and size of the drive cam may be engineered using methods well know to those of skill in the art resulting in a even more optimal design. The shape and size of the main cam may be engineered using methods well know to those of skill in the art resulting in an even more optimal design. The shape and size of the cams may be optimized for the manufacturing process and may differ from the drawings.

FIGS. 14 through 20 illustrate different exemplary stages of the invention when being used to walk upon inclined or declined surfaces.

FIGS. 21 through 31 illustrate different exemplary stages of walking having controlled plantarflexion using neutralizing springs as embodied in the invention.

Figure 32:
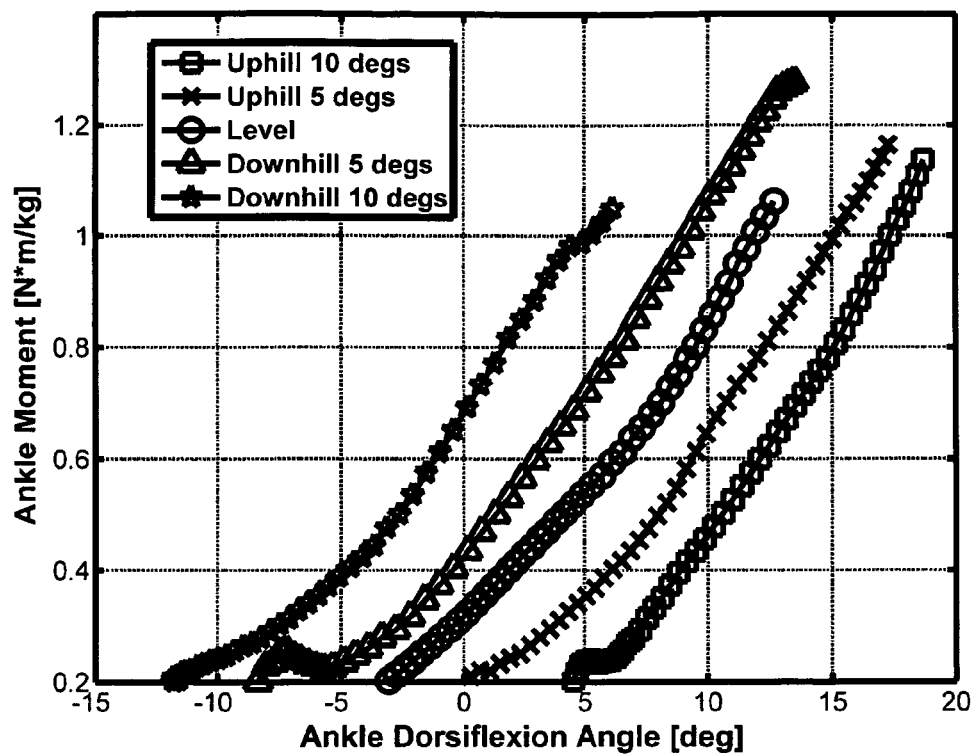
FIG. 32 illustrates a series of experimental data obtained during testing of a device of the invention on inclined, level, and declined surfaces.

FIG. 32 illustrates experimental data from one subject having unilateral transtibial amputation. FIG. 32 shows that the torque curve of the invention used in a single gait on a variety of inclined, level, and declined surfaces shifts to the left (negative) as predicted above in FIG. 6.

FIGS. 34 through 40 illustrate preferred embodiments of the invention.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

We claim:

1. An improved passive adaptive ankle-foot prosthesis comprising a footplate, a housing pivotally connected to the footplate, a first cam connected to the footplate, a second cam for engagement with the first cam, a bracket pivotally secured to the housing so as to be attachable to a leg, wherein the bracket is fixedly attached to the second cam, wherein the second cam is in movable contact with a part of the first cam, the first cam and second cam comprising a cam clutch system, and wherein the footplate comprises an anterior plantar portion and a posterior portion, a torsion member associated with the footplate, and the posterior portion of the footplate comprising an aperture shaped and adapted to confine at least one neutralizing element and a spacer, the neutralizing element being operatively connected to the spacer and the spacer is connected to the housing.

2. The ankle-foot prosthesis of claim 1 further comprising a second neutralizing element.

3. The ankle-foot prosthesis of claim 2, wherein the neutralizing element comprises an elastomeric material.

4. The ankle-foot prosthesis of claim 1 wherein the torsion member comprises an elastomeric material.

5. The ankle-foot prosthesis of claim 1 wherein the neutralizing element and the cam clutch are in-line.

6. The ankle-foot prosthesis of claim 1 wherein the prosthesis comprises a composition selected from the group consisting of stainless steel, copper, aluminum, titanium, metal matrix composite, metal alloy, NITINOL, DELRIN (acetal), acrylonitrile butadiene styrene (ABS), nylon, polypropylene, polybromate, polycarbonate, glycolised polyethylene terephthalate (PETg) copolyester, polytetrafluorethylene (PTFE), PTFE, polypropylene, a polymer, glass fiber-resin composites, and carbon fiber resin composites.

7. The ankle-foot prosthesis of claim 1, wherein the first cam comprises an external surface and an internal surface.

8. The ankle-foot prosthesis of claim 7, wherein the second cam is in movable contact with the internal surface of the first cam.

9. The ankle-foot prosthesis of claim 8 wherein the range of movable contact of the second cam in contact with the first cam is not greater than 95°.

10. The ankle-foot prosthesis of claim 1, wherein the prosthesis has a plantarflexion-dorsiflexion range of from between 80° plantarflexion to about 45° dorsiflexion.

11. The ankle-foot prosthesis of claim 1, further comprising a foot shell.

12. The ankle-foot prosthesis of claim 1, further comprising means for attachment to a leg selected from the group consisting of a residual limb socket, direct skeletal attachment to the residual limb, and a leg cuff.

13. The ankle-foot prosthesis of claim 1 wherein the torsion member is interposed between the first cam and the footplate.

14. The ankle-foot prosthesis of claim 1 wherein the first cam is pivotally connected to the footplate coaxially with the housing.

15. The ankle-foot prosthesis of claim 1 wherein the prosthesis is configured for placement on at least one side of an ankle of a user and further comprising means for attachment to the ankle selected from the group consisting of a residual limb socket, direct skeletal attachment, a clamshell socket, a leg cuff, and a hinge bar in combination with a hinge spring.

16. An ankle-foot prosthesis comprising:
a footplate with an elongated anterior portion and a posterior portion;
a triceps surae spring associated with the footplate to bias the footplate toward a plantarflexed position;
an ankle frame pivotally connected to the posterior portion of the footplate at a first pivot point;
a neutralizing spring interposed between the ankle frame and the footplate for biasing the ankle frame to a neutral position;
a main cam secured to the footplate for engagement with the triceps surae spring;
a pylon pivotally secured to the ankle frame and including a cam engagement link having a drive cam mounted thereto for engagement with the main cam; and
a hinge spring interposed between the pylon and the ankle frame biased to disengage the drive cam from the main cam.

17. The ankle-foot prosthesis of claim 16 wherein the main cam is pivotally secured to the footplate at a second pivot point and the first pivot point and the second pivot point are coincident.

* * * * *

UNITED STATES PATENT AND TRADEMARK OFFICE
CERTIFICATE OF CORRECTION

PATENT NO.         : 8,480,760 B2
APPLICATION NO.    : 13/066361
DATED              : July 9, 2013
INVENTOR(S)        : Andrew H. Hansen et al.

It is certified that error appears in the above-identified patent and that said Letters Patent is hereby corrected as shown below:

IN THE SPECIFICATION:

DELETE LINES 18 - 21 ON PAGE ONE OF THE SPECIFICATION (COL. 1) AND REPLACE WITH THE FOLLOWING:

"This invention was made with government support under United States Department of Veterans Affairs' grant numbers A6567R and A6565R. The United States government has certain rights in the invention."

--This invention was made with government support grant numbers A6565R and A6567R awarded by the United States of America Department of Veterans Affairs. The government has certain rights in the invention.--

Column 6, line 20 – "Cain" should be --Cam--

Column 8, line 13 – "pylori" should be --pylon--

Column 10, line 11 – "pylori" should be --pylon--

Column 13, lines 51, 54, 60, and 63 – "pylori" should be --pylon--

Column 15, line 1 – "know" should be --known--

Signed and Sealed this
First Day of April, 2014

Michelle K. Lee
*Deputy Director of the United States Patent and Trademark Office*